US007008644B2

(12) United States Patent
Batycky et al.

(10) Patent No.: US 7,008,644 B2
(45) Date of Patent: Mar. 7, 2006

(54) METHOD AND APPARATUS FOR PRODUCING DRY PARTICLES

(75) Inventors: Richard P. Batycky, Newton, MA (US); Blair C. Jackson, Quincy, MA (US); Lloyd P. Johnston, Belmont, MA (US); Jeffrey D. Mintzes, Brighton, MA (US); Ernest E. Penachio, Cambridge, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 327 days.

(21) Appl. No.: 10/101,563

(22) Filed: Mar. 20, 2002

(65) Prior Publication Data

US 2003/0180283 A1 Sep. 25, 2003

(51) Int. Cl.
*A61K 9/14* (2006.01)
(52) U.S. Cl. ...................................... 424/489
(58) Field of Classification Search ................ 424/489
See application file for complete search history.

(56) References Cited

U.S. PATENT DOCUMENTS

| 3,185,580 | A | 5/1965 | Hanrahan et al. |
| 4,540,602 | A | 9/1985 | Motoyama et al. |
| 4,828,181 | A | 5/1989 | Singels-Craenen |
| 6,077,543 | A | 6/2000 | Gordon et al. |
| 6,423,345 | B1 * | 7/2002 | Bernstein et al. |

FOREIGN PATENT DOCUMENTS

| DE | 100 47 341 C1 | 2/2002 |
| EP | 0 299 757 A2 | 1/1989 |
| EP | 0 312 610 A1 | 4/1989 |
| EP | 1 136 068 A2 | 9/2001 |
| FR | 80 241 | 3/1963 |
| GB | 279 544 | 10/1927 |
| GB | 676 432 | 7/1952 |
| GB | 2 278 603 | 12/1994 |
| WO | 98/29096 | * 7/1998 |
| WO | WO-WO 98/29096 A1 | 7/1998 |
| WO | WO 99/16419 A1 | 4/1999 |
| WO | WO 99/32083 | 7/1999 |
| WO | WO 0010541 | 3/2000 |
| WO | WO-WO 00/10541 | 3/2000 |
| WO | WO 02/111695 A2 | 2/2002 |
| WO | WO-WO 03/000202 A2 | 1/2003 |

OTHER PUBLICATIONS

Gaβmann, Peter et al., "Hydrosols—Alternatives for the Parenteral Application of Poorly Water Soluble Drugs," European Journal of Pharmaceutics and Biopharmaceutics, 40(2): 64-72 (1994).
Vanbever, Rita et al., "Formulation and Physical Characterization of Large Porous Particles for Inhalation," Pharmaceutical Research, 16(11): 1735-1742 (1999).

* cited by examiner

*Primary Examiner*—Thurman K. Page
*Assistant Examiner*—Humera N. Sheikh
(74) *Attorney, Agent, or Firm*—Andrea G. Reister; Covington & Burling

(57) ABSTRACT

Method and apparatus for producing dry particles. Two liquid components are combined in a static mixer, atomized into droplets, and the droplets dried to form dry particles. Use of the static mixer enables incompatible liquid components to be rapidly and homogeneously combined. The present invention optimizes process conditions for increasing and controlling particle porosity. The present invention also allows for optimization of particle size in real-time during particle production.

6 Claims, 10 Drawing Sheets

METHOD AND APPARATUS FOR PRODUCING DRY PARTICLES

BACKGROUND OF THE INVENTION

1. Field of the Invention

The present invention relates to a method and apparatus for producing dry particles. More particularly, the present invention relates to a method and apparatus for producing dry particles that are suitable for inhalation into the lung, and which contain an active agent.

2. Related Art

Delivery of drugs and other active agents can be accomplished through the use of dry powder compositions made from particles containing the drug or active agent. In producing such particles, it is often desirable to combine substances with significantly different physical properties to achieve the desired pharmaceutical effect in patients. Moreover, it is often desirable to produce particles that are a combination of different substances. One way to produce particles containing a combination of different substances is to dissolve the substances in suitable solvents, and then remove the solvents by, for example, evaporation or drying, to yield the desired particles. A major difficulty with this approach is that substances with differing physical properties often have very different solubilities in solvents. Consequently, co-solvents, or a larger mixture of solvents, may be needed to form the solution from which the particles are produced. However, the use of co-solvents can cause degradation of one of the components, through chemical or physical incompatibility of the components in solution.

One example of the incompatibility of components is the production of particles that contain a hydrophobic component and a hydrophilic component. The production of such particles is described in U.S. Pat. No. 6,077,543 to Gordon et al. ("the Gordon patent"). As described in the Gordon patent, a hydrophobic drug solution and a hydrophilic excipient solution are spray dried together to form dry powders containing the drug and the excipient. To solve the incompatibility between the hydrophobic and hydrophilic components, the hydrophilic and hydrophobic components are separately dissolved in different solvents, and separately directed simultaneously through a nozzle into a spray dryer. In this method, the two liquid components are separately delivered to the nozzle that atomizes the two liquid components into droplets that are dried in a spray dryer to form dry particles.

One of the drawbacks of the method and apparatus of the Gordon patent is that there is no complete mixing of the two liquid components before being atomized into droplets. Thus, the droplets that are produced are unlikely to be a homogeneous mixture of the two liquid components, nor is there likely to be uniformity among the droplets. Consequently, the particles that are produced are unlikely to contain a homogeneous mixture of the drug and excipients, and are unlikely to have uniformity among the particles themselves. Thus, there is a need in the art for an improved method and apparatus for producing dry particles that contain a homogenous mixture of drug and excipient components, with improved uniformity among the particles. There is a particular need in the art for such a method and apparatus where the drug component and excipient component are physically or chemically incompatible in the liquid state.

One important application for dry powder compositions is pulmonary drug delivery. Several properties of the dry particles have been identified that correlate with enhanced delivery to the pulmonary system. For example, it has been found that particles having a tap density less than 0.4 g/cm$^3$ and an aerodynamic diameter that is between about 1 and about 3 microns ($\mu$m) are well suited for delivery to the alveoli or the deep lung. If delivery to the central or upper airways is desired, particles having larger aerodynamic diameters, ranging for example, from about 3 to about 5 microns are preferred. Furthermore, particles having a geometric diameter greater than about 5 microns are believed to more successfully avoid phagocytic engulfment by alveolar macrophages and clearance from the lungs.

There is a need in the art for improved methods for producing particles having selected geometric and aerodynamic sizes optimized for delivery to targeted sites of the pulmonary system. There is a particular need for an apparatus and method that allows for optimization of particle size in real-time, during the particle production process.

The apparatus and method of the present invention, a description of which is fully set forth below, solve the aforementioned problems and difficulties with conventional approaches to producing dry powder compositions.

SUMMARY OF THE INVENTION

The present invention is directed to a method and apparatus for producing dry particles. The dry particles are advantageously formed into dry powder compositions that can be administered to a patient, such as a human patient, for therapeutic purposes. In a preferred aspect of the present invention, the dry powder compositions are formulated for inhalation by a patient for delivery of an active agent through the pulmonary system.

In one aspect of the present invention, a method for preparing a dry powder composition is provided. In such a method, a hydrophilic component and a hydrophobic component are prepared, one of which comprises an active agent. The hydrophobic and hydrophilic components are combined in a static mixer to form a combination. The combination is atomized to produce droplets, which are dried to form dry particles. In a preferred aspect of this method, the atomizing step is performed immediately after the components are combined in the static mixer. In another preferred aspect of this method, the hydrophilic component comprises an active agent that may include, for example, insulin, albuterol sulfate, L-DOPA, humanized monoclonal antibody (for example, IgG1), human growth hormone (hGH), epinephrine, and ipatropium bromide monohydrate.

In a further aspect of the present invention, a method for preparing a dry powder composition is provided. In such a method, first and second components are prepared, one of which comprises an active agent. The first and second components are combined in a static mixer to form a combination. The first and second components are such that combining them causes degradation in one of the components. In a preferred aspect, the active agent is incompatible with the other component. The combination is atomized to produce droplets that are dried to form dry particles. In a preferred aspect of such a method, the first component comprises an active agent dissolved in an aqueous solvent, and the second component comprises an excipient dissolved in an organic solvent.

In yet a further aspect of the present invention, a method for preparing a dry powder composition is provided. In such a method, a first phase is prepared that comprises human growth hormone, sodium phosphate, and ammonium bicarbonate. A second phase is prepared that comprises ethanol. The first and second phases are combined in a static mixer to form a combination. The combination is atomized to produce droplets that are dried to form dry particles. In another aspect of such a method, the second phase further comprises 1,2-dipahnitoyl-sn-glycero-3-phosphatidylcholine (DPPC). In a further aspect of such a method, the resulting dry particles consist of about 93 wt % human growth hormone and about 7 wt % phosphate. In still a further aspect of such a method, the resulting particles consist of about 79 wt % human growth hormone, about 7 wt % phosphate, and about 14 wt % DPPC.

In still a further aspect of the present invention, a method for preparing a dry powder composition is provided. In such a method, a hydrophilic component is combined with an organic solvent in a static mixer to form a combination. The combination is atomized to produce droplets that are dried to form dry particles. In a preferred aspect of such a method, the hydrophilic component comprises an active agent. In a further aspect of such a method, the hydrophilic component further comprises an excipient.

In yet a further aspect of the present invention, an apparatus for preparing a dry powder composition is provided. The apparatus includes a static mixer having an inlet end and an outlet end. The static mixer is operative to combine an aqueous component with an organic component to form a combination. Means are provided for transporting the aqueous component and the organic component to the inlet end of the static mixer. An atomizer is in fluid communication with the outlet end of the static mixer to atomize the combination into droplets. The droplets are dried in a dryer to form dry particles. In one aspect of the present invention, the atomizer is a rotary atomizer. Such a rotary atomizer may be vaneless, or may contain a plurality of vanes. In a further aspect of the present invention, the atomizer is a two-fluid mixing nozzle. Such a two-fluid mixing nozzle may be an internal mixing nozzle or an external mixing nozzle. In one aspect of the present invention, the means for transporting the aqueous and organic components are two separate pumps. Alternatively, a single pump could be used. In a further aspect, the apparatus also includes a geometric particle sizer that determines a geometric diameter of the dry particles, and an aerodynamic particle sizer that determines an aerodynamic diameter of the dry particles.

In still a further aspect of the present invention, a method for preparing dry particles having a selected volume median geometric diameter is provided. Such a method comprises:
   drying atomized liquid droplets to form dry particles;
   selecting a particle density ($\rho$);
   measuring a measured mass median aerodynamic diameter ($d_a^m$) of the dry particles;
   measuring a measured volume median geometric diameter ($d_g^m$) of the dry particles;
   calculating a calculated volume median geometric diameter ($d_g^e$) from the particle density and the measured mass median aerodynamic diameter from the equation $d_a^m = d_g^c \sqrt{\rho}$; and adjusting the particle density until the calculated volume median geometric diameter is substantially equal to the measured volume median geometric diameter.

In another aspect of such a method, the adjusting step comprises:
   comparing the calculated volume median geometric diameter to the measured volume median geometric diameter to determine a differential; and
   responsive to the differential, changing a particle density value in an aerodynamic particle sizer.

In still another aspect of such a method, a liquid feed is atomized to form the atomized liquid droplets. In a preferred aspect, a first liquid component and a second liquid component are combined in a static mixer to form the liquid feed.

In yet a further aspect of the present invention, a system for preparing dry particles having a selected geometric diameter is provided. The system includes a dryer that dries liquid droplets to form dry particles. The system also includes a geometric particle sizer coupled to the dryer that determines a measured geometric diameter ($d_g^m$) of the dry particles. The system also includes an aerodynamic particle sizer coupled to the dryer that determines a measured aerodynamic diameter ($d_a^m$) of the dry particles responsive to a density ($\rho$) of the dry particles. A further component of the system is a processor coupled to the aerodynamic particle sizer. The processor is responsive to a program configured for calculating a calculated geometric diameter ($d_g^e$) from the density and the measured aerodynamic diameter from the equation $d_a^m = d_g^c \sqrt{\rho}$, and adjusting the density until the calculated geometric diameter is substantially equal to the measured geometric diameter. In a further aspect of such a system, the program is configured to carry out the adjusting by comparing the calculated geometric diameter to the measured geometric diameter to determine a differential, and, responsive to the differential, changing the density used by the aerodynamic particle sizer. In a further aspect of such a system, an atomizer is coupled to the dryer to atomize a liquid feed to form the liquid droplets. In still a further aspect of such a system, a static mixer is in fluid communication with the atomizer, the static mixer combining a first liquid component and a second liquid component to form the liquid feed.

Features and Advantages

It is a feature of the present invention that a static mixer is used to combine two liquid components to form a combination that is atomized into droplets that are dried to form particles. The static mixer advantageously provides rapid and homogeneous mixing of the two liquid components. This is particularly advantageous when the two liquid components are physically and/or chemically incompatible with each other. Because of the homogeneous mixing provided by the static mixer, the particles resulting from use of the apparatus and method of the present invention advantageously have substantially the same composition at the particle scale.

It is a further feature of the present invention that the liquid feed solution to be atomized is fully mixed prior to atomization. The present invention also advantageously minimizes the time that the liquid feed solution to be atomized remains in its combined state prior to atomization.

Another feature of the present invention is that it can be used to produce particles that contain a hydrophilic active agent, and hydrophilic or hydrophobic excipients.

Another feature of the present invention is that it can be used to produce dry particles that are particularly well adapted for inhalation into the lung, particularly the deep lung. As one example, the present invention advantageously optimizes process conditions for increasing and controlling particle porosity. As another example, the formulations of the present invention advantageously include ammonium bicarbonate that increases particle porosity. As yet another example, the present invention provides a method and apparatus that can be used to optimize particle size in real-time during the particle production process. In this manner, process conditions for particles of selected geometric and/or aerodynamic size can advantageously be optimized using a minimal amount of material.

BRIEF DESCRIPTION OF THE FIGURES

The present invention is described with reference to the accompanying drawings. In the drawings, like reference numbers indicate identical or functionally similar elements. The left most digit(s) of a reference number indicates the figure in which the reference number first appears.

DETAILED DESCRIPTION OF THE PREFERRED EMBODIMENTS

Overview

Figure 1A:
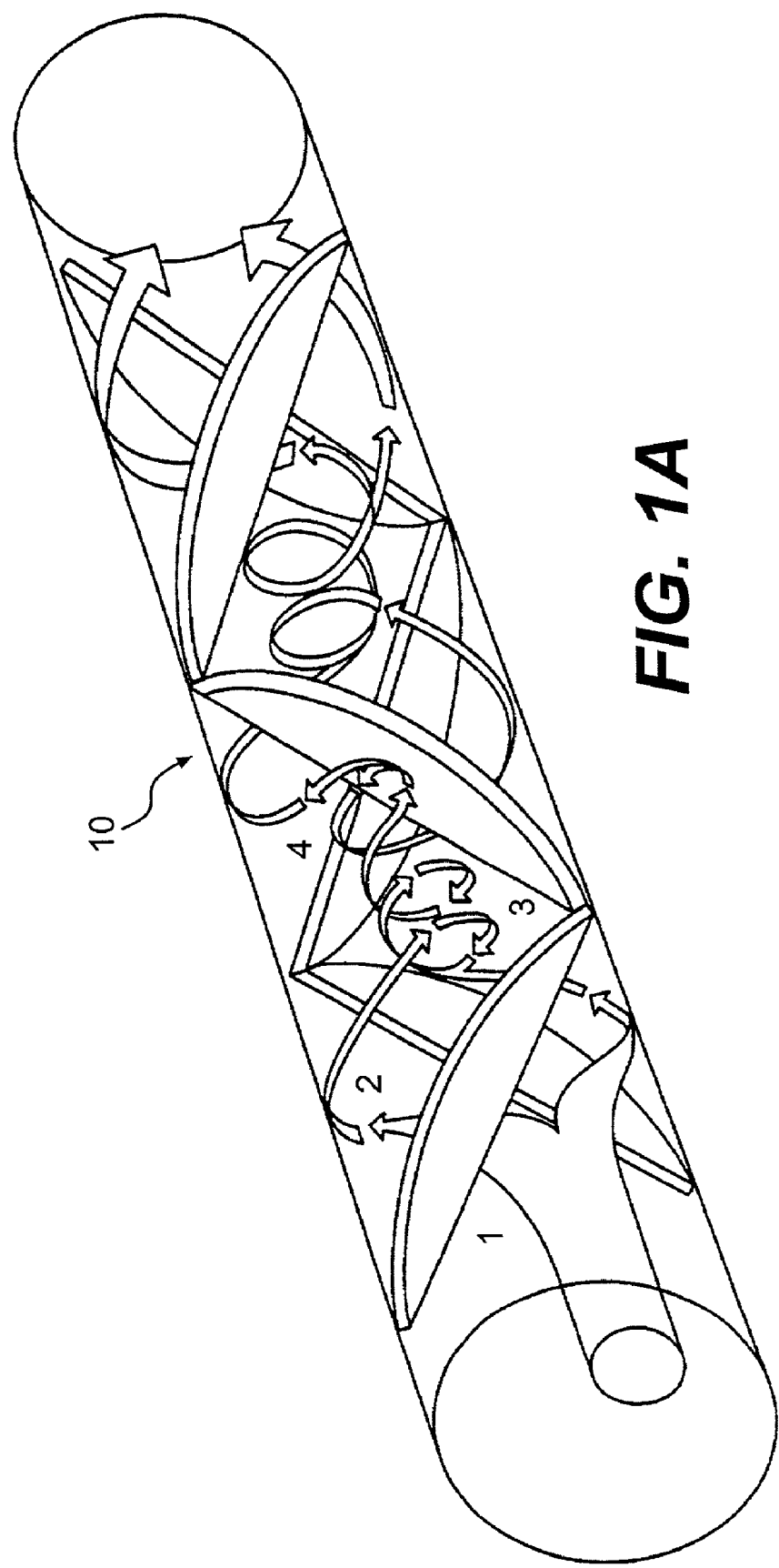
FIG. 1A illustrates flow through a static mixer

The present invention is directed to apparatus and methods for preparing dry particles. The present invention has particular applicability for preparing dry particles, and dry powder compositions, for inhalation into the lung for therapeutic purposes. Particularly, preferred dry particles include those described and disclosed in the following eight applications filed on even date herewith: "Inhalable Sustained Therapeutic Formulations," Appl. No. 60/366,479. filed Mar. 20, 2002; "Inhalable Salmeterol and Ipratropium Compositions," Appl. No. 60/366,449, filed Mar. 20, 2002; "Inhalable Salmeterol and Ipratropium Compositions," Appl. No. 60/366,354, filed Mar. 20, 2002; "Inhalable Salmeterol and Ipratropium Compositions," Appl. No. 60/366,470, filed Mar. 20, 2004; "Inhalable Salmeterol and Ipratropium Compositions," Appl. No. 60/366,487, filed Mar. 20, 2002; "Inhalable Salmeterol and Ipratropium Compositions," Appl. No. 60/366,440, filed Mar. 20, 2002; "hGH (Human Growth Hormone) Formulations for Pulmonary Administration," Appl. No. 60/366,488, filed Mar. 20, 2002; "Pulmonary Delivery for LevoDOPA," Appl. No. 60/366,471, filed Mar. 20, 2002, the entirety of each of which is incorporated herein by reference. The description that follows will provide examples of preparing such dry particles. However, it should be understood by one skilled in the art that the present invention is not limited to preparing dry particles, or dry powder compositions, suitable for inhalation into the lung, and that dry particles for other purposes can be prepared. As used herein, the term "dry" refers to particles that have a moisture and/or residual solvent content such that the powder is physically and chemically stable in storage at room temperature, and is readily dispersible in an inhalation device to form an aerosol. Typically, the moisture and residual solvent content of the particles will be below 10 wt %, usually below 5 wt % or lower.

The present invention solves the problems associated with preparing dry particles that contain incompatible components by providing a method and apparatus that ensures a homogeneous mixture of the components in the finished dry particle product, and improves uniformity among the particles themselves. As used herein, "incompatible components" refers to components that may be chemically or physically incompatible with each other when in contact. One example of incompatible components is a protein in aqueous solution in which the protein is stable, and an organic solution containing hydrophobic substances. The aqueous protein solution is incompatible with the hydrophobic organic solution since the organic solution will cause degradation of the protein. In the method of the present invention, the incompatible components, such as a hydrophilic component and a hydrophobic component, are prepared and maintained separately from each other until just prior to the particle production process. The term "hydrophobic component" refers to materials that are insoluble or sparingly or poorly soluble in water. Such compositions typically have a solubility below 5 mg/ml, usually below 1 mg/ml, in water. The term "hydrophilic component" refers to materials that are highly soluble in water. Typical aqueous solubilities of hydrophilic components will be greater than 5 mg/ml, usually greater than 50 mg/ml, and can be greater than 100 mg/ml. The incompatible hydrophobic and hydrophilic components are combined in a static mixer to form a combination that is a homogeneous mixture of the incompatible components. Immediately thereafter, the combination is atomized into droplets that are dried to form the dry particles. Through the use of the static mixer, the incompatible components can be very rapidly combined into a homogeneous mixture. The use of the static mixer significantly reduces the amount of time the incompatible components are in contact with each other, thereby minimizing or eliminating the degradation effects resulting from such contact. The use of the static mixer also ensures a complete mixing of the incompatible components before atomization so that each droplet, and thus each finished dry particle, has substantially the same composition. Uniformity in the composition of the particles at the particle scale is a significant factor in the efficacy of the dry particles when used for therapeutic purposes.

When preparing dry particles and dry powder compositions for inhalation, it is desirable to increase the porosity of the particles so that the particles can be inhaled into the lung, preferably into the deep lung. The present invention advantageously optimizes process conditions for increasing and controlling particle porosity. In a preferred embodiment of the present invention, an internal mixing two-fluid nozzle is used to atomize a liquid feed stream to form atomized droplets. In an internal mixing two-fluid nozzle, one or more gas streams impinge upon a liquid feed stream to atomize the liquid feed stream into atomized droplets that exit the nozzle. Such a nozzle allows for intimate contact between the gas (such as nitrogen) and the liquid feed stream. This increases the amount of gas in the liquid feed stream and the resulting droplets. When the droplets are dried, the exiting gas contributes to the porosity of the finished dry particles. Increased gas in the droplets can also be achieved through the use of ammonium bicarbonate, or other volatile salts, in the liquid feed stream.

If dry particles are being produced for inhalation into the lung, then it is important to control the size of the particles during the production process. The particles can be characterized by aerodynamic diameter ($d_a$) and geometric diameter ($d_g$). Aerodynamic diameter can be determined using a "time-of-flight" measurement system that accelerates the particles being measured past two points. The time of travel is measured, and correlated to an aerodynamic size through the following relationship: $d_a = d_g \sqrt{\rho}$, where $\rho$ is the density of the particles. A suitable device for determining aerodynamic diameter is an aerodynamic particle sizer, such as the APS Model 3321, available from TSI, Inc., St. Paul, Minn.

Such a device measures the mass median aerodynamic diameter (MMAD) of the particles, as well as complete particle size distributions (PSD).

Laser diffraction techniques can be used to determine particle geometric diameter. One such device is the Insitec online particle sizer, available from Malvern Instruments Ltd. The Insitec device consists of an optical sensor head, a signal processing unit, and a computer for instrument control and data collection and analysis. The Insitec device measures volume median geometric diameter (VMGD) of the particles in real-time as they are produced. In addition to VMGD, the Insitec device generates complete particle size distributions (PSD), which allows an operator to visually determine the polydispersity of the particles being generated.

Through the apparatus and method of the present invention, optimization of particle size is accomplished in real-time during particle production. In the process of the present invention, the density ($\rho$) of the particles is used as an optimization variable. The density of the particles is adjusted until the measured geometric diameter is equal to the geometric diameter calculated from the equation $d_a = d_g \sqrt{\rho}$. One significant advantage of this method is that the liquid stream to be atomized and dried into particles needs to be sprayed for only about three minutes to collect sufficient data to optimize the process variables. This allows for the rapid screening of multiple process conditions using a minimal amount of material. Moreover, the total length of spraying time and material required is significantly reduced.

The size distribution of airborne particles can be measured through gravimetric analysis through the use of, for example, an Andersen Cascade Impactor (ACI), Anderson Instruments, Smyrna, Ga. The ACI is a multi-stage device that separates aerosols into distinct fractions based on aerodynamic size. The size cutoffs of each stage are dependent upon the flow rate at which the ACI is operated. For the examples and discussion herein, a flow rate of 60 L/min is used, unless indicated otherwise.

At each stage of the ACI, an aerosol stream passes through a series of nozzles, and impinges upon an impaction plate. Particles with sufficient inertia impact the plate, while those with insufficient inertia to impact the plate remain in the aerosol stream, and are carried to the next stage. Each successive stage has a higher aerosol velocity in the nozzle so that smaller diameter particles are collected at each successive stage. Particles too small to be collected on the last stage are collected on a collection filter.

A two-stage ACI is particularly advantageous for characterizing and optimizing dry particles for inhalation. The first fraction is referred to as "FPF(5.6)", or Fine Particle Fraction (5.6). This fraction corresponds to the percentage of particles having an aerodynamic diameter of less than 5.6 $\mu$m. The fraction of the particles that passes this stage and is deposited on the collection filter is referred to as "FPF(3.4)", or Fine Particle Fraction (3.4). This fraction corresponds to the percentage of particles having an aerodynamic diameter of less than 3.4 $\mu$m. FPF(5.6) has been demonstrated to correlate to the fraction of the dry particles that is capable of inhalation into the lung of a patient. FPF(3.4) has been demonstrated to correlate to that fraction that is capable of reaching the deep lung of a patient. The foregoing correlations provide a quantitative indicator that can be used with the process of the present invention to optimize the production process and the resulting finished dry particles for inhalation into the lung.

Apparatus and Methods of the Present Invention

The apparatus and methods of the present invention will now be described with reference to the accompanying figures. As will be described below in more detail with respect to FIG. 2, a static mixer is used to combine two liquid components to form a combination. The combination is atomized to produce droplets that are dried to form dry particles. In one embodiment of the present invention, the two liquid components are a hydrophilic component and a hydrophobic component. In another embodiment, the two components are such that combining the two causes degradation in one of the components. In yet another embodiment, one component is a hydrophilic component and the other component is an organic solvent.

Static or motionless mixers consist of a conduit or tube in which is received a number of static mixing elements. Static mixers provide uniform mixing in a relatively short length of conduit, and in a relatively short period of time. With static mixers, the fluid moves through the mixer, rather than some part of the mixer, such as a blade, moving through the fluid. Flow through one embodiment of a static mixer is illustrated in FIG. 1A. A pump (not shown) introduces a stream of one or more fluids into an inlet end of a static mixer 10 as shown generally at 1. The stream is split and forced to opposite outside walls as shown generally at 2. A vortex is created axial to the centerline of static mixer 10, as shown generally at 3. The vortex is sheared and the process recurs, but with the opposite rotation, as shown generally at 4. The clockwise/counter-clockwise motion ensures a homogeneous product that exits an outlet end of static mixer 10.

Figure 1B:
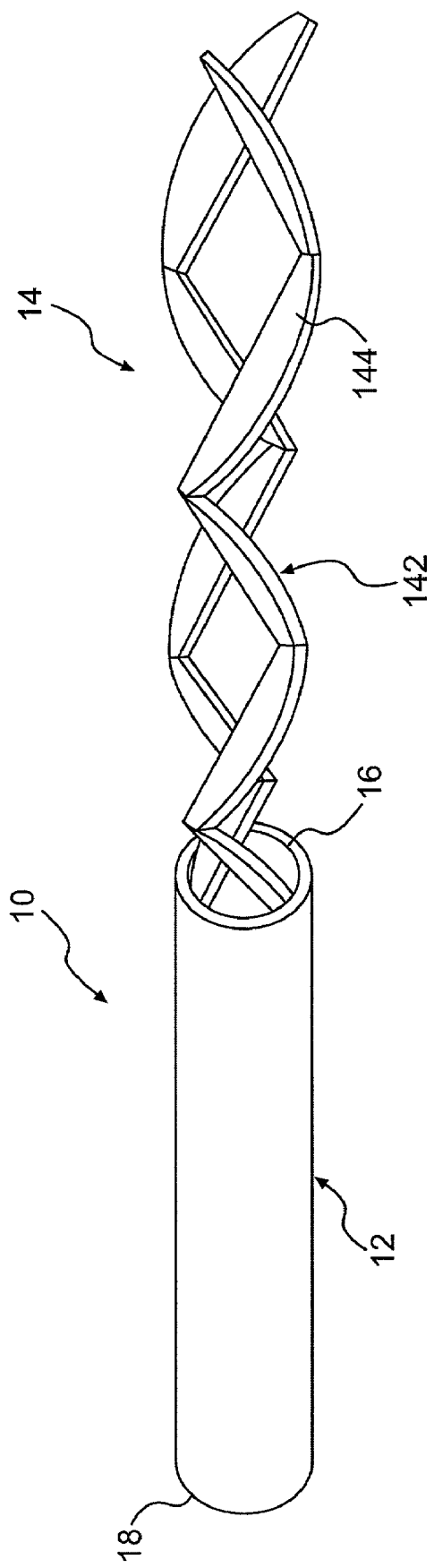
FIG. 1B shows a static mixer suitable for use with the present invention.

One embodiment of a static mixer is shown in FIG. 1B. Static mixer 10 includes a number of stationary or static mixing elements 14 arranged in a series within a conduit or pipe 12. The number of elements can range from, for example, 4 to 32 or more. Conduit 12 is circular in cross-section and open at opposite ends for introducing (inlet end 18) and withdrawing (outlet end 16) fluids. Mixing element 14 comprises segments 142. Each segment 142 consists of a plurality of generally flat plates or vanes 144. The two substantially identical segments 142 are preferably axially staggered with respect to each other. A static mixer as shown in FIG. 1B is more fully described in U.S. Pat. No. 4,511,258, the entirety of which is incorporated herein by reference.

Figure 2:
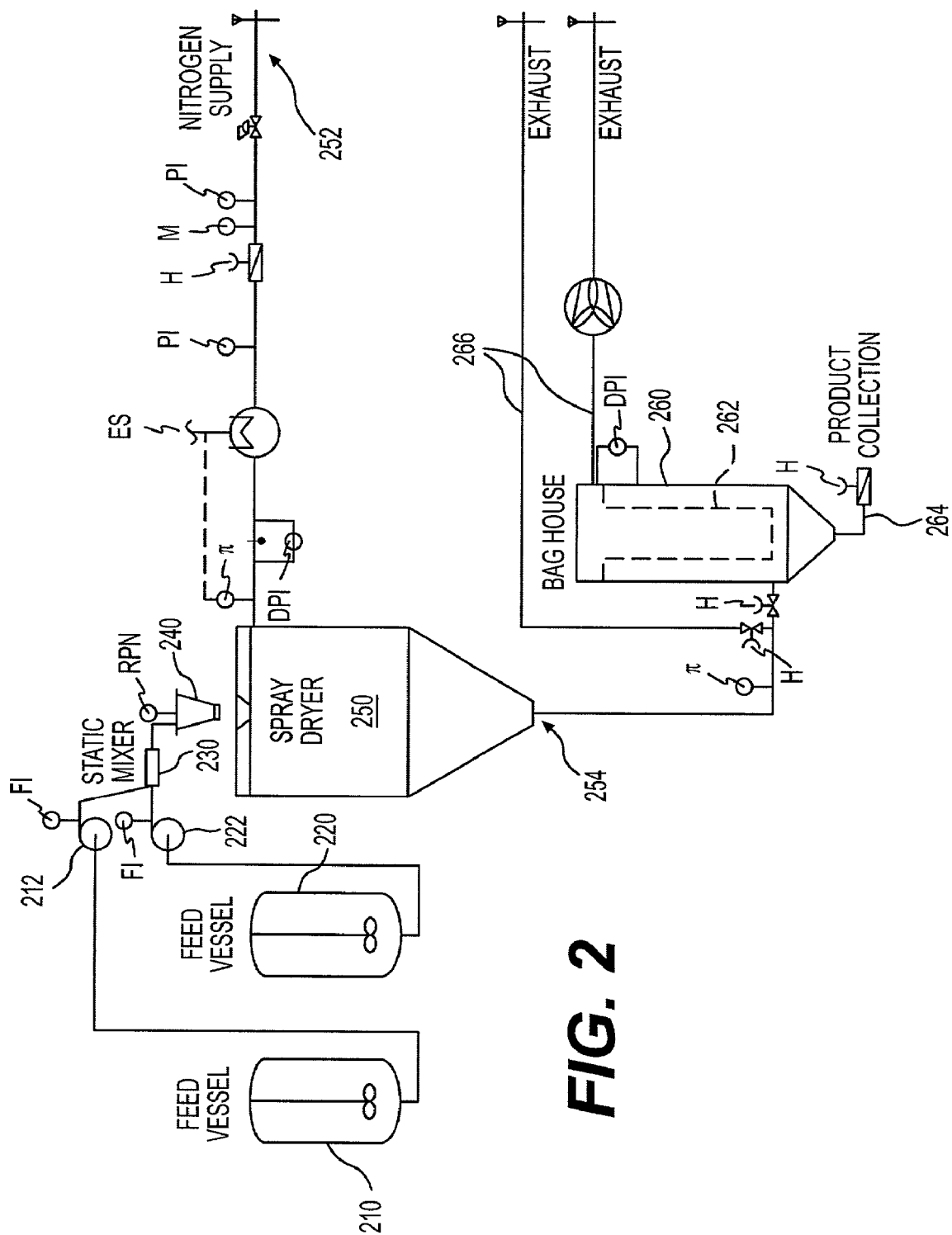
FIG. 2 illustrates one embodiment of a system of the present invention for producing dry particles.

Turning now to FIG. 2, one embodiment of a system of the present invention for producing dry particles is shown. The system includes a first feed vessel 210 and a second feed vessel 220. As will be explained in more detail below with respect to the various examples, feed vessel 210 can contain, for example, a hydrophilic component, an aqueous solution, or other suitable liquid component. Feed vessel 220 can contain, for example, a hydrophobic component, an organic solution, or other suitable liquid component. The contents of feed vessel 210 and feed vessel 220 are transported, via suitable means, to an inlet end of a static mixer 230. In one embodiment of the present invention, the means for transporting is a first pump 212 for the contents of feed vessel 210, and a second pump 222 for the contents of feed vessel 220. Alternatively, a single pump could be used to transport the contents of feed vessels 210 and 220 to the inlet end of static mixer 230. As would be readily apparent to one skilled in the art, other means for transporting the contents of feed vessels 210 and 220 could be used. In one embodiment of the present invention, feed vessels 210 and 220 contain the same volume of liquid, and pumps 212 and 222 are operated at substantially the same rate. In other embodiments, pumps 212 and 222 are operated at different rates. Pumps 212 and 222 may be gear pumps, or other types of pumps as would be apparent to one skilled in the art.

The contents of feed vessels 210 and 220 are combined in static mixer 230 to form a combination. The combination is a homogeneous mixture of the liquid components entering the inlet end of static mixer 230. As illustrated in FIG. 2, static mixer 230 may be oriented in a horizontal configuration, i.e., a central axis of static mixer 230 is perpendicular to a central axis of a spray dryer 250. Preferably, static mixer 230 is oriented in a vertical configuration, as shown, for example, in FIG. 6 (discussed in more detail below). Static mixers suitable for use with the present invention are illustrated in FIGS. 1A and 1B, and include model 1/4-21, made by Koflo Corporation.

An outlet end of static mixer 230 is in fluid communication with an atomizer 240. Atomizer 240 atomizes the combination flowing out of static mixer 230 into droplets. Because the combination flowing out of static mixer 230 is a homogeneous mixture of the input liquid components, the droplets formed by atomizer 240 will also contain a homogeneous mixture of the input liquid components. Atomizers suitable for use with the present invention include, but are not limited to, rotary atomizers, two-fluid mixing nozzles, and pressure, ultrasonic, vibrating plate, and electrostatic nozzles, and combinations of the foregoing. Atomizers suitable for use with the present invention will be described in more detail below with respect to FIGS. 3–5.

In a preferred embodiment of the present invention, the combination formed in static mixer 230 is atomized immediately after the combination is formed. That is, the outflow of static mixer 230 flows into atomizer 240 for atomization. This is particularly advantageous when first feed vessel 210 and second feed vessel 220 contain incompatible components since the contact between the incompatible components will be minimized.

The droplets formed by atomizer 240 are dried in spray dryer 250 to form dry particles. Because the droplets formed by atomizer 240 contain a homogeneous mixture of the input liquid components, the dry particles formed by spray dryer 250 will also contain a homogeneous mixture of the input liquid components. Spray dryers suitable for use with the present invention include a Mobile Minor, EX Model manufactured by Niro, Columbia, Md. Other commercially available spray dryers from suppliers such as Niro, APV Systems, Denmark (e.g., the APV Anhydro Model), and Swenson, Harvey, Ill., also can be employed, as can scaled-up spray dryers suitable for industrial capacity production lines.

A drying gas is used in spray dryer 250 to dry the droplets to form dried particles. Examples of gases suitable for use with the present invention include, but are not limited to, air, nitrogen, argon, carbon dioxide, helium, and combinations or mixtures thereof. In a preferred embodiment, nitrogen gas is used. As illustrated in FIG. 2, a nitrogen gas supply 252 is coupled to spray dryer 250, through suitable valves and regulators as would be apparent to one skilled in the art.

A bag house 260 is coupled to an outlet end 254 of spray dryer 250. Disposed within bag house 260 is a bag filter 262. A gas-solid stream, made up of the drying gas and the dry particles, exits outlet end 254. Exhaust lines 266 provide exhaust for spray dryer 250 and bag house 260. The gas-solid stream exiting spray dryer 250 enters bag house 260. Bag filter 262 retains the dry particles, and allows the hot gas stream, containing the drying gas and evaporated water and solvents, to pass. Preferably, bag filter 262 is made from a material such as Gore-Tex®, available from W. L. Gore & Associate, Inc., Newark, Del. Dry particles are collected at a product collection point 264 by running a back pulse of nitrogen across bag filter 262.

The collected particles can then be screened, for example, using size screening methods known to one skilled in the art. In one embodiment of the present invention, single dosages of the collected dry particles are measured, and the single dosages are then packaged, using techniques well known to one skilled in the art. In this manner, a unit dose of a dry powder composition can be formed by placing a therapeutically effective amount of dry powder composition made up of particles into a unit dose receptacle.

Figure 3:
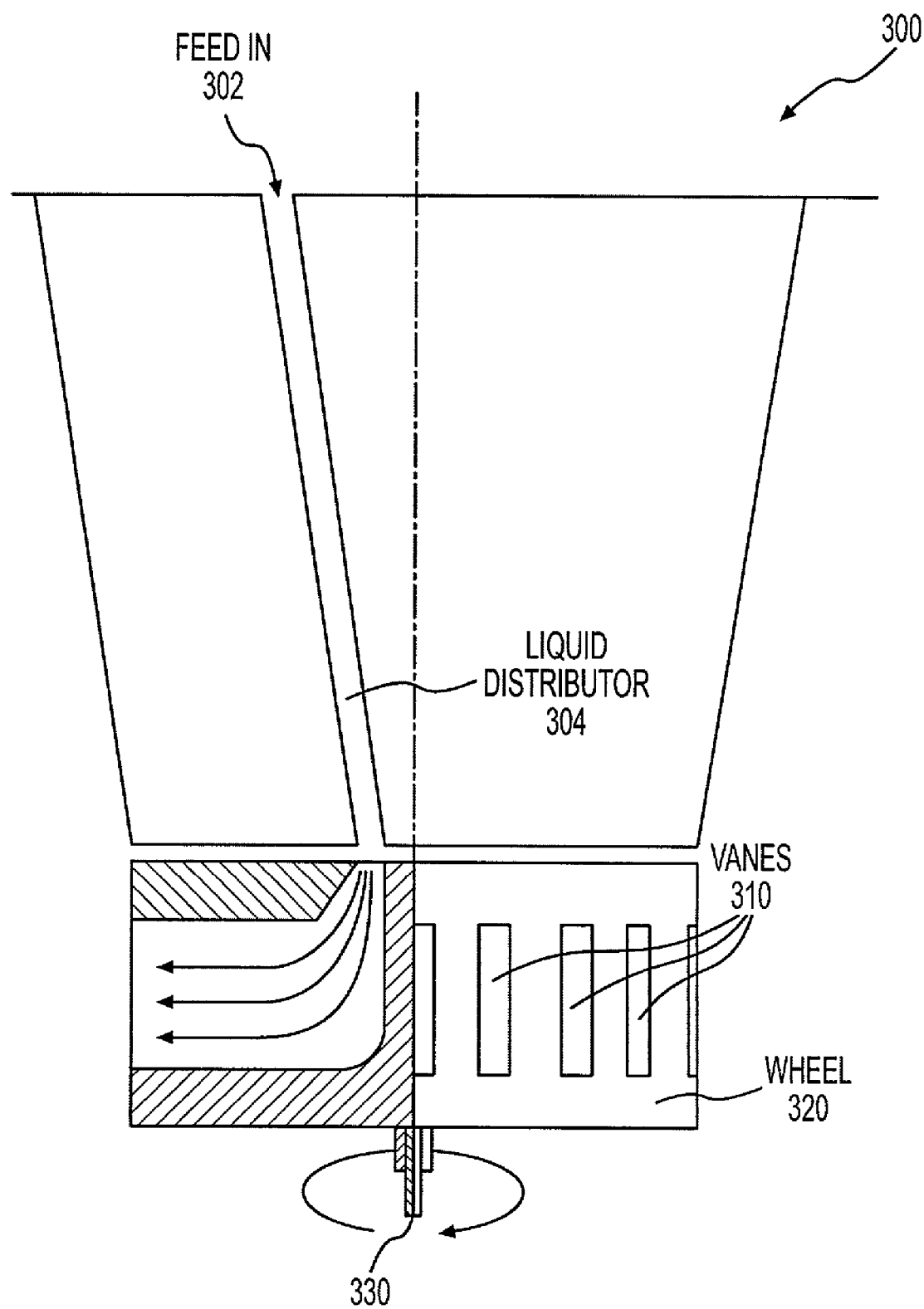
FIG. 3 shows a vaned rotary atomizer suitable for use with the present invention.

One embodiment of an atomizer suitable for use with the system depicted in FIG. 2 is a vaned rotary atomizer, such as rotary atomizer 300 illustrated in FIG. 3. Rotary atomizer 300 includes a spinning wheel 320 that spins about an axis 330. Liquid feed enters rotary atomizer 300 at an inlet point 302, and is distributed across wheel 320, as depicted generally at 304. Wheel 320 disperses the liquid feed into a spray of fine droplets. The spin rate of the wheel is controlled, as is the liquid feed rate. By controlling the spin rate and liquid feed rate, the characteristics of the spray can be controlled, such as droplet size. Rotary atomizer 300 is configured with 24 vanes 310. It should be readily apparent to one skilled in the art that rotary atomizers with other number of vanes 310 can be used with the present invention. For example, a rotary atomizer having 4 vanes, or a vaneless rotary atomizer, could also be used.

Figure 4:
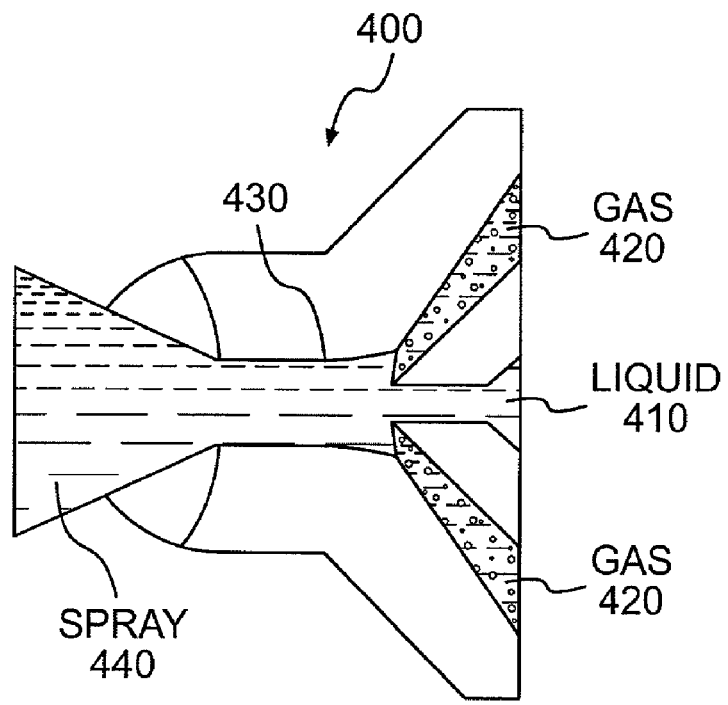
FIG. 4 illustrates one embodiment of an internal mixing nozzle suitable for use with the present invention.
Figure 5:
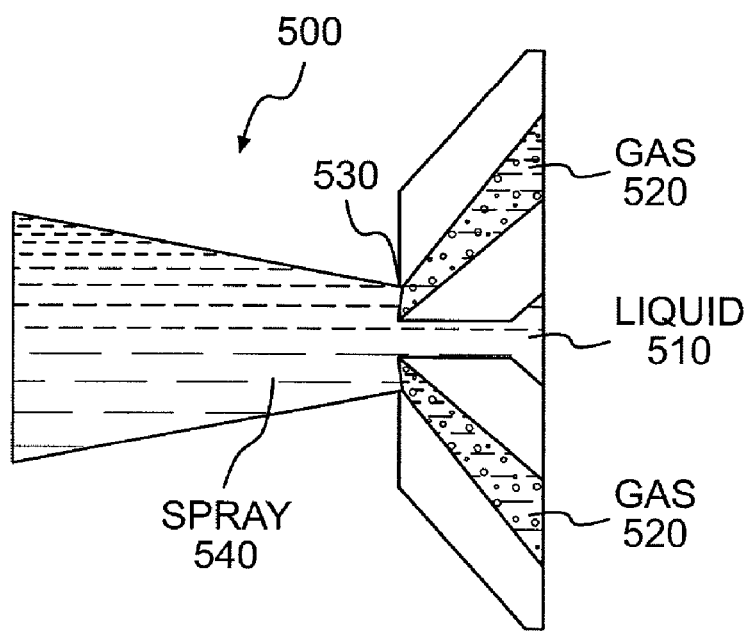
FIG. 5 illustrates one embodiment of an external mixing nozzle suitable for use with the present invention.

Alternate embodiments of an atomizer suitable for use with the system shown in FIG. 2 are shown in FIGS. 4 and 5. FIGS. 4 and 5 depict two-fluid nozzles that atomize a liquid feed stream through the use of one or more gas streams that impinge upon the liquid feed stream. An internal mixing nozzle 400 is illustrated in FIG. 4. In internal mixing nozzle 400, two gas streams 420 impinge on a liquid feed stream 410 in a mixing chamber 430 that is internal to internal mixing nozzle 400. A spray of atomized droplets 440 exits internal mixing nozzle 400. As would be apparent to one skilled in the art, other numbers of gas streams, including a single gas stream, could be used.

FIG. 5 depicts an external mixing nozzle 500. In external mixing nozzle 500, two gas streams 520 impinge on a liquid feed stream 510 in a mixing zone 530 that is adjacent to the external edge of external mixing nozzle 500. A spray of atomized droplets 540 is formed external to external mixing nozzle 500. As would be apparent to one skilled in the art, other numbers of gas streams, including a single gas stream, could be used.

In order to produce particles optimized for inhalation and pulmonary drug delivery, optimization experiments were conducted to enhance porosity during the atomization step of the dry particle production process. Through these experiments it was determined that changing the mode of atomization affects porosity, and that porosity can be controlled through the selection of the type of atomizer.

Three rotary atomizers were tested, all of which had a configuration substantially as shown in FIG. 3. The three atomizers differed in the number of vanes 310 on wheel 320. One had four vanes ("V4"), one had 24 vanes ("V24"), and one was vaneless. The V4 and the V24 wheels were operated using similar process conditions, shown below in Table 1, to obtain particles with similar geometric sizes, shown below in Table 2. Because of the increased number of vanes, the V24 wheel could not be operated at as a high an rpm as the V4 wheel.

TABLE 1

| Atomizer Wheel | Inlet Temperature (° C.) | Outlet Temperature (° C.) | Atomizer Speed (rpm) | Drying Gas Pressure (mmH$_2$O) | Feed Rate (mL/min) |
|---|---|---|---|---|---|
| V4 | 120 | 55 | 50000 | 98 | 63 |
| V24 | 120 | 62 | 34000 | 110 | 60 |

TABLE 2

| Run Number | Wheel Type | Geometric Size Measured @ | | | | Fine Particle Fraction (%) | |
|---|---|---|---|---|---|---|---|
| | | 0.5 bar | 2 bar | 3 bar | 4 bar | <5.6 µm | <3.4 µm |
| 294053 | V4 | 9.5 | 8.9 | 8 | 6.7 | 72 | 56 |
| 294054 | V24 | 9.2 | 7.5 | 6.5 | 5.3 | 65 | 48 |

The data in Table 2 suggest that particles produced using the V4 wheel are larger and more porous (e.g., have higher FPF(5.6) and FPF(3.4)) than particles produced using the V24 wheel. One reason for this difference could be differences in "air pumping" between the two atomizers. "Air pumping" occurs with rotary atomizers because, as the wheels spin, the wheels act as a fan, drawing air through the wheel. At the flow or feed rates to the atomizers typically used with the present invention, the V24 vanes do not completely fill with liquid. Consequently, there is a path for the air to flow over the liquid in the vane, with only a portion being entrained in the liquid to be atomized. The V4 vanes operate similarly, but because the vanes are physically smaller, the V4 vanes are usually filled with liquid during operation. Consequently, the air and atomization gas must both pass simultaneously through the vane, rather than over the vane. This allows for a more intimate contact between the air and liquid to be atomized. This intimate contact between gas and liquid induces more porosity in the resulting dry particle.

The increase of porosity in the particles resulting from the gas/liquid contact can be seen by comparing the particles produced with vaned atomizers with particles produced using a vaneless atomizer. Vaneless atomizers do not generate a strong air pumping effect. A V4 and a vaneless atomizer were operated using similar process conditions, shown below in Table 3. As can be seen from Table 4, the particles produced using the vaneless atomizer were both smaller and more dense (lower FPF(5.6) and FPF(3.4)) than the particles produced using the V4 atomizer.

TABLE 3

| Atomizer Wheel | Inlet Temperature (° C.) | Outlet Temperature (° C.) | Atomizer Speed (rpm) | Drying Gas Pressure (mmH$_2$O) | Feed Rate (mL/min) |
|---|---|---|---|---|---|
| V4 | 155 | 63 | 60000 | 98 | 52.5 |
| Vaneless | 155 | 63 | 50000 | 98 | 52.5 |

TABLE 4

| Run Number | Wheel Type | Geometric Size Measured @ | | | | Fine Particle Fraction (%) | |
|---|---|---|---|---|---|---|---|
| | | 0.5 bar | 2 bar | 3 bar | 4 bar | <5.6 µm | <3.4 µm |
| 294088 | V4 | 14.2 | 12.5 | 11.2 | 9.9 | 70 | 55 |
| 294089 | Vaneless | 5.4 | 5 | 4.8 | 4.2 | 63 | 40 |

In a preferred embodiment of the present invention, a two-fluid nozzle is used to increase the contact between gas and liquid during the atomization step to increase the porosity of the resulting dry particles. As described above, a two-fluid nozzle is configured to allow for mixing of two fluids, such as a gas and a liquid, during atomization. The mixing can occur either externally (using, for example, a nozzle such as that shown in FIG. 5) or internally (using, for example, a nozzle such as that shown in FIG. 4) with respect to the nozzle itself.

Experiments were conducted with an external mixing nozzle substantially as shown in FIG. 5 at nozzle or system pressures ranging from 15 to 40 psi. As shown below in Table 5, the FPF(5.6) ranged from 76 to 81% and the FPF(3.4) ranged from 59 to 63%. Changes in porosity as a function of increasing gas rates were not observed with external mixing nozzles.

TABLE 5

| Run Number | System Nozzle Pressure (psi) | Geometric Size Measured @ | | | | Fine Particle Fraction (%) | |
|---|---|---|---|---|---|---|---|
| | | 0.5 bar | 2 bar | 3 bar | 4 bar | <5.6 µm | <3.4 µm |
| 294141 | 15 | 9.4 | 8.4 | 7.3 | 5.3 | 81 | 63 |

TABLE 5-continued

| Run Number | System Nozzle Pressure (psi) | Geometric Size Measured @ | | | | Fine Particle Fraction (%) | |
|---|---|---|---|---|---|---|---|
| | | 0.5 bar | 2 bar | 3 bar | 4 bar | <5.6 μm | <3.4 μm |
| 294132C | 20 | 9.5 | 7.5 | 6.7 | 4.9 | 77 | 61 |
| 294132B | 40 | 8.4 | 9.4 | 7.1 | 6.4 | 76 | 59 |

Experiments were conducted using an internal mixing nozzle substantially as shown in FIG. 4. Use of internal mixing nozzles likely allows for more intimate contact between the liquid and gas, thereby resulting in dry particles having higher porosity, as evidenced by higher FPF(5.6) and FPF(3.4). Experiments were conducted to test the effect of nozzle pressure and the effect of the mass flow ratio of gas to liquid. As evidenced by the data in Table 6 below, more porous particles can be obtained at higher operating pressures with an internal mixing nozzle. The pressure effect may be a reflection of the higher gas/liquid ratio of run 294152A (1.8) compared to that of run 294151 (1.3). As evidenced by the data in Table 7 below, more porous particles can be obtained at higher gas:liquid flow rates with an internal mixing nozzle. The operating conditions for use with an internal mixing nozzle that optimized the geometric size and the porosity/fine particle fraction are shown below in Table 8.

As noted above, the present invention advantageously optimizes process conditions for increasing and controlling the porosity of the dry particles through the use of the internal mixing two-fluid nozzle. In another aspect of the present invention, particle porosity is increased through the use of volatile salts. Carbonation of one of the liquid components used to form the dry particles induces porosity in the resulting dried particles by nucleation of carbon dioxide ($CO_2$). The nucleation of $CO_2$ induces multiple phases (gas and liquid) in an atomized droplet, with the gas phase being inaccessible for the excipients. Such heterogeneous nature of the atomized droplet leads to increased porosity in the resulting dry particle once drying is complete. The tap density of the dry particles can be used as a measure of porosity. The more porous the dry particles, the lower the observed tap density. It has been found that particles spray dried from a carbonated formulation solution have much lower tap density than particles spray dried from an otherwise identical solution.

TABLE 6

| Run Number | System Nozzle Pressure (psi) | Geometric Size Measured @ | | | | Fine Particle Fraction (%) | |
|---|---|---|---|---|---|---|---|
| | | 0.5 bar | 2 bar | 3 bar | 4 bar | <5.6 μm | <3.4 μm |
| 294151 | 68 | 12 | 10.3 | 8.8 | 7.2 | 76 | 64 |
| 294152A | 100 | 11.5 | 8.8 | 8.3 | 7.4 | 86 | 79 |

TABLE 7

| Run Number | Gas/Liquid Ratio | Geometric Size Measured @ | | | | Fine Particle Fraction (%) | |
|---|---|---|---|---|---|---|---|
| | | 0.5 bar | 2 bar | 3 bar | 4 bar | <5.6 μm | <3.4 μm |
| 294150A | 1 | 12.9 | 12.3 | 10.1 | 8.1 | 76 | 64 |
| 294150C | 1.5 | 14 | 11.8 | 9.8 | 7.8 | 82 | 70 |

TABLE 8

| Run Number | Gas/Liquid Ratio | System Nozzle Pressure (psi) | Geometric Size Measured @ | | | | Fine Particle Fraction (%) | |
|---|---|---|---|---|---|---|---|---|
| | | | 0.5 bar | 2 bar | 3 bar | 4 bar | <5.6 μm | <3.4 μm |
| 342012B | 1.9 | 58 | 10.8 | 10.4 | 8 | 6.5 | 90 | 81 |

An experiment was conducted using a formulation of 60/18/18/4 (DPPC/Lactose/Albumin/Albuterol sulfate). Four batches were prepared. The aqueous phase of two batches were sparged with $CO_2$, the other two were not treated with $CO_2$. The spray dry conditions were well controlled for all four batches so that they were operated at the same process condition. A vaned rotary atomizer (V24) was used in this experiment. The results are shown in Table 9 below.

TABLE 9

| Batch No. | Sparging $CO_2$ | Inlet T (° C.) | Outlet T (° C.) | Feed Rate (ml/min) | Atomizer Speed (rpm) | Tap Density (g/cc) |
|---|---|---|---|---|---|---|
| 1 | No | 110 | 56–57 | 40 | 18000 | 0.09 |
| 2 | Yes | 110 | 56–57 | 40 | 18000 | 0.065 |

TABLE 9-continued

| Batch No. | Sparging $CO_2$ | Inlet T (° C.) | Outlet T (° C.) | Feed Rate (ml/min) | Atomizer Speed (rpm) | Tap Density (g/cc) |
|---|---|---|---|---|---|---|
| 3 | No | 110 | 56–57 | 40 | 18000 | 0.091 |
| 4 | Yes | 110 | 56–57 | 40 | 18000 | 0.059 |

From the data shown in Table 9 above, it is quite clear that particles manufactured by the solution sparged with $CO_2$ have lower tap density, with a more porous structure. Therefore, sparging the spray drying solution with $CO_2$ helps to increase porosity of the particles.

In a preferred aspect of the present invention, increased porosity, and consequently lower tap density, can be achieved through the use of ammonium bicarbonate ($NH_4HCO_3$) in one of the liquid components used to form the dry particles. In an alternate embodiment of the present invention, carbonation of one of the liquid components, or of the combination solution, could be achieved by sparging with $CO_2$ at reduced temperature (4° C.) or pressurizing with $CO_2$, also preferably at reduced temperature. The carbonate components ($HCO_3^-/CO_3^{2-}/CO_2$) would not remain in the final dry particles as they are volatile species. They would be eliminated during the drying process. Use of carbonate components or other volatile salts have the advantage of avoiding the use of higher temperatures for inducing porosity. Additionally, carbonate components can advantageously be used over mild pH ranges where protein stability is maximized. Moreover, the pH of the resulting dry particles can be adjusted through the addition of appropriate counter ions.

As described above, the addition of volatile salts to the solution used to form dry particles increases the porosity of the particles. The addition of volatile salts also increases the production of insoluble complexes, the production of which can be used to control the release rate of the active agent in the particles, both proteins and small molecules. The formation of an insoluble complex begins with the interaction between, for example, two species when they are dissolved together. In solution, molecules of opposite charge are attracted to each other via electrostatic forces. When the ionic species are limited to oppositely charged forms A and B, then A and B will attract to each other. If A and B interact strongly enough, they are likely to form an insoluble complex $A_xB_y$, where x and y are the stoichiometric coefficients describing the ratio(s) with which A and B tend to associate. This complex can stay in suspension, or may form a precipitate that will settle or flocculate. If additional ionic species are present, the additional species will compete with A and B on a charge basis and tend to reduce the strength of the interaction between A and B, thereby decreasing the tendency of A and B to form an insoluble complex. If the additional ionic species can be selectively removed, A and B will then form an insoluble complex.

Insoluble material can interfere with the production of large porous particles that are of particular utility for pulmonary drug delivery. It is often desirable to have large porous particles that contain species A and B, where A and B have the tendency to form an insoluble complex $A_xB_y$. Higher ionic strength decreases the strength of the interaction between A and B, rendering A and B more soluble in the process solution. As the material is spray dried, the volatile salt is preferentially removed from the droplets as the dry particles are formed. The insoluble complex $A_xB_y$ may subsequently form in the nearly-dried particles, but the porous structure has already formed in those particles.

The following non-limiting examples illustrate the use of ammonium bicarbonate to produce particles having a low aerodynamic diameter, which results in a low tap density and high porosity. It should be understood by one skilled in the art that the present invention is not limited to the use of ammonium bicarbonate, and that other suitable volatile salts could also be used without departing from the scope of the invention.

EXAMPLES

Porous Bovine Albumin Particles 350 mg of bovine serum albumin, 100 mg of anhydrous sodium citrate, 66 mg of calcium chloride dihydrate, and 10 g of ammonium bicarbonate were dissolved in 500 mL of sterile water. The resulting feed solution was spray dried using a Niro spray dryer equipped with a rotary atomizer. The drying gas (dry nitrogen) was delivered at a flow rate of approximately 100 kg/h with a 170° C. inlet temperature, and a 61° C. outlet temperature. The feed solution was delivered to the atomizer/spray dryer at 60 ml/min liquid flow rate. The atomizer was operated at 29,000 rpm, with −2 inches of water pressure in the spraying chamber of the spray dryer. The resulting dry particles had a mass mean aerodynamic diameter of 4.03 µm, and a volume mean geometric diameter of 7.76 µm at 1 bar.

48 mg of bovine serum albumin, 20 mg of anhydrous sodium citrate, 13 mg of calcium chloride dihydrate, 28 mg of maltodextrin (M100) and 10 g of ammonium bicarbonate were dissolved in 1000 mL of sterile water. The resulting feed solution was spray dried using a Niro spray dryer equipped with a rotary atomizer. The drying gas (dry nitrogen) was delivered at a flow rate of approximately 100 kg/h with a 170° C. inlet temperature, and a 56° C. outlet temperature. The feed solution was delivered to the atomizer/spray dryer at 60 ml/min liquid flow rate. The atomizer was operated at 29,000 rpm, with −2 inches of water pressure in the spraying chamber of the spray dryer. The resulting dry particles had a mass mean aerodynamic diameter of 3.97 µm, and a volume mean geometric diameter of 15.01 µm at 1 bar.

Porous Humanized IgG Antibody Particles 47.35 ml of 50.7 mg/ml humanized monoclonal IgG1 antibody solution was added to 1000 mL water (pH=6.4). 1.6 g of DPPC was added to 1000 mL isopropyl alcohol. The two solutions were mixed by slowly adding the ethanol solution to the aqueous solution immediately prior to spray drying. The resulting feed solution was spray dried using a Niro spray dryer equipped with a rotary atomizer. The drying gas (dry nitrogen) was delivered at a flow rate of approximately 110 kg/h with a 100° C. inlet temperature, and a 45° C. outlet temperature. The feed solution was delivered to the atomizer/spray dryer at 50 ml/min liquid flow rate. The atomizer was operated at 34,500 rpm, with −2 inches of water pressure in the spraying chamber of the spray dryer. The resulting dry particles had a mass mean aerodynamic diameter of 3.01 µm, and a volume mean geometric diameter of 9.17 µm at 1 bar.

Porous Human Growth Hormone Particles 2.63 g hGH, 1.03 g sucrose, 1.58 g leucine, 368 mg sodium phosphate, 26.25 mg Tween-20, and 52.5 g ammonium bicarbonate was added to 3675 mL water (pH=7.4). 1575 mL of ethanol was slowly added to the aqueous solution immediately prior to spray drying. The resulting feed solution was spray dried using a Niro spray dryer equipped with a rotary atomizer. The drying gas (dry nitrogen) was delivered at a flow rate of approximately 110 kg/h with a 139° C. inlet temperature, and a 62° C. outlet temperature. The feed solution was delivered to the atomizer/spray dryer at 60 ml/min liquid flow rate. The atomizer was operated at 34,000 rpm, with −5 inches of water pressure in the spraying chamber of the spray dryer. The resulting dry particles had a mass mean aerodynamic diameter of 1.94 μm, and a volume mean geometric diameter of 5.8 μm at 1 bar.

Particles containing 93 wt % hGH and 7 wt % sodium phosphate were prepared as follows. The aqueous solution was prepared by adding 328 mg of sodium phosphate monobasic to 400 mL of water for irrigation (Braun). The pH was adjusted to 7.4 using 1.0 N NaOH. 15 g of ammonium bicarbonate (Spectrum Chemicals) was added to the sodium phosphate buffer. 200 mL of ethanol (Pharmco) was added to complete the aqueous solution. The aqueous solution was combined in a static mixer with 400 mL of 14 g/L hGH solution (5.6 g hGH dissolved in sodium phosphate buffer at pH=7.4). The combined solution was spray dried under the following process conditions:

- Inlet temperature~115° C.
- Outlet temperature from the drying drum~70° C.
- Nitrogen drying gas=110 kg/hr
- Nitrogen atomization gas=46 g/min
- 2 Fluid internal mixing nozzle atomizer
- Nitrogen atomization pressure~65 psi
- Liquid feed rate=25 ml/min
- Liquid feed temperature~22° C.
- Pressure in drying chamber=−2.0 in water The resulting particles had a FPF(5.6) of 84%, and a FPF(3.4) of 77%, both measured using a 2-stage ACI. The volume mean geometric diameter was 8.9 μm at 1.0 bar.

Porous Albuterol Sulfate Particles 80 mg of albuterol sulfate, 460 mg of maltodextrin, 350 mg of leucine, 110 mg of Pluronic F68, and 10 g of ammonium bicarbonate were dissolved in 500 mL of sterile water. The aqueous solution was mixed with 500 mL of ethanol. The resulting feed solution was spray dried using a Niro spray dryer equipped with a rotary atomizer. The drying gas (dry nitrogen) was delivered at a flow rate of approximately 100 kg/h with a 150° C. inlet temperature, and a 62° C. outlet temperature. The feed solution was delivered to the atomizer/spray dryer at 65 ml/min liquid flow rate. The atomizer was operated at 22,000 rpm, with 39 mm of water pressure in the spraying chamber of the spray dryer. The resulting dry particles had a mass mean aerodynamic diameter of 3.33 μm, and a volume mean geometric diameter of 11.5 μm at 4 bar.

Porous Danazol Particles 800 mg of danazol, 1.6 g of maltodextrin, 1.2 g leucine, 400 mg of polyethyleneglycol (PEG) 1500, and 40 g of ammonium bicarbonate were dissolved in 2 L of sterile water. The aqueous solution was mixed with 2 L of ethanol. The resulting feed solution was spray dried using a Niro spray dryer equipped with a rotary atomizer. The drying gas (dry nitrogen) was delivered at a flow rate of approximately 100 kg/h with a 155° C. inlet temperature, and a 64° C. outlet temperature. The feed solution was delivered to the atomizer/spray dryer at 70 ml/min liquid flow rate. The atomizer was operated at 22,000 rpm, with 39 mm of water pressure in the spraying chamber of the spray dryer. The resulting dry particles had a mass mean aerodynamic diameter of 2.69 μm, and a volume mean geometric diameter of 10.6 μm at 4 bar.

Figure 6:
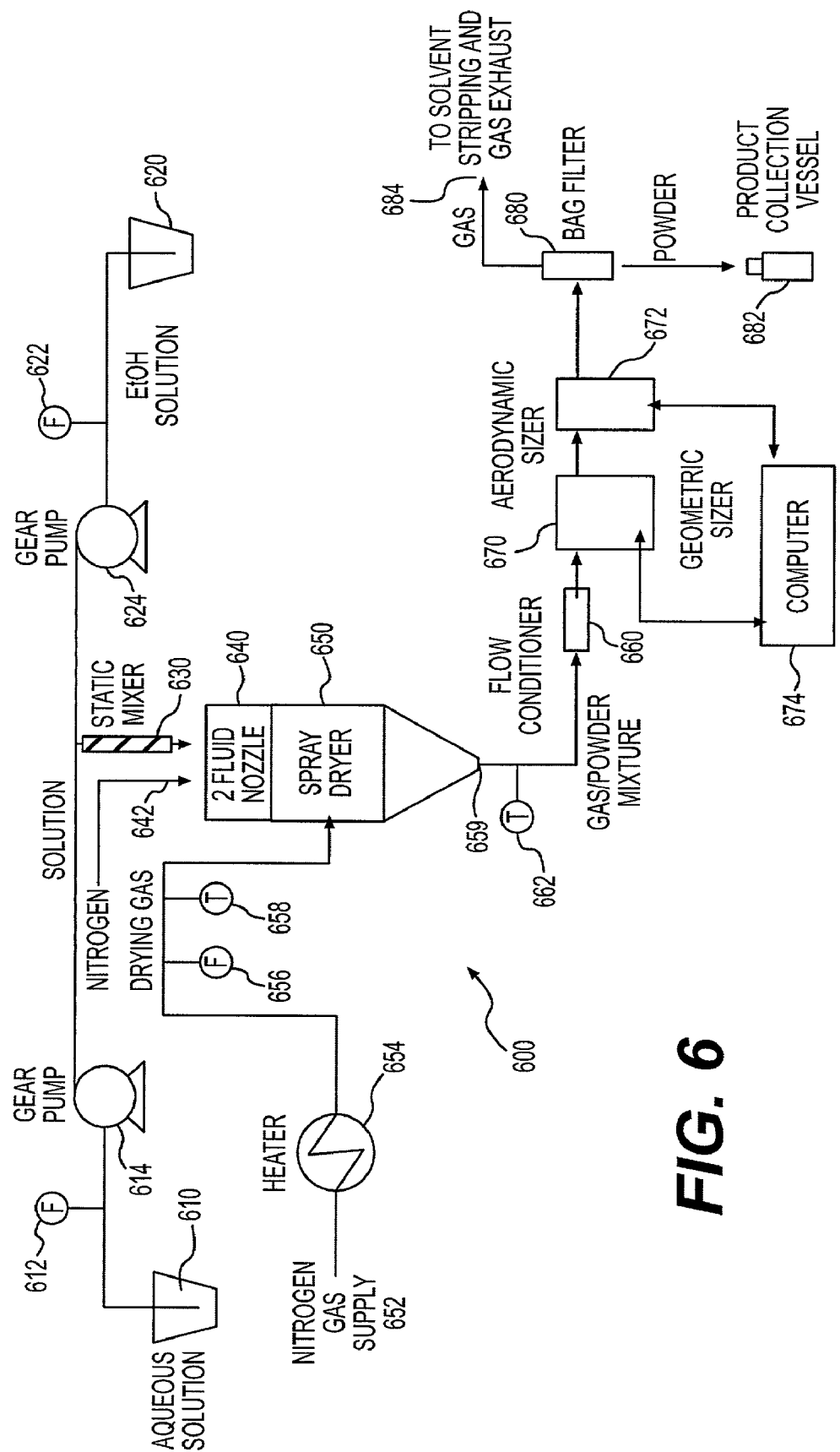
FIG. 6 illustrates an alternate embodiment of a system of the present invention for producing dry particles.

Turning now to FIG. 6, an alternate embodiment of a system 600 for producing dry particles is shown. System 600 will be explained for the exemplary situation of combining an aqueous solution 610 with an ethanol solution 620 to form dry particles. As would be readily apparent to one skilled in the art, system 600 is not limited to use of an aqueous solution and an ethanol solution. For example, system 600 could be used to combine other hydrophilic and hydrophobic components, other aqueous and organic components, or a hydrophilic component and an organic solvent, to form dry particles. System 600 could also be used to combine two components to form dry particles where the combination of the two components causes degradation in one of the components.

As illustrated in FIG. 6, aqueous solution 600 is transported via a gear pump 614 and a flow meter 612 to a static mixer 630. Ethanol (EtOH) solution 620 is transported via a gear pump 624 and a flow meter 622 to static mixer 630. In one embodiment of the present invention, the same volume of aqueous solution 610 and ethanol solution 620 is used, and pumps 614 and 624 are operated at substantially the same rate to deliver the respective solutions to static mixer 630 at substantially the same rate. In other embodiments, pumps 614 and 624 are operated at different rates. As would be apparent to one skilled in the art, the concentration of components in the final dry particles can be used to determine the pump rates for pumps 614 and 624. For example, in one embodiment of the present invention, the volumes of aqueous solution 610 and ethanol solution 620 are selected to each be completely consumed during the spray drying process. In such an embodiment, the pump rates for pumps 614 and 624 are selected so that solutions 610 and 620 are both used up. As would be appreciated by one skilled in the art, other types of pumps, or other means for transporting the solutions to static mixer 630 could be used. Alternatively, a single pump could be used to deliver both solutions to static mixer 630. In the embodiment shown in FIG. 6, static mixer 630 is oriented in a vertical configuration, i.e., a central axis of static mixer 630 is parallel to a central axis of a spray dryer 650. Alternatively, static mixer 630 could be configured in an inclined configuration, at an acute angle with respect to the central axis of spray dryer 650. The inclined or vertical configuration of static mixer 630 helps ensure laminar flow, with any bubbling or gassing at the top. Preferably, the inputs to the static mixer flow upwards to provide more homogeneous mixing, and to prevent channeling. Static mixers suitable for use with the present invention are illustrated in FIGS. 1A and 1B, and include model 1/4-21, made by Koflo Corporation.

An outlet end of static mixer 630 is in fluid communication with a two-fluid nozzle 640 that is used to atomize the combination flowing out of static mixer 630 into droplets. In an alternative embodiment of system 600, a rotary atomizer, such as rotary atomizer 300 depicted in FIG. 3, is used in place of nozzle 640. Because the combination flowing out of static mixer 630 is a homogeneous mixture of the input liquid components (aqueous solution and ethanol solution), the droplets formed by nozzle 640 will also contain a homogeneous mixture of the input liquid components. Nozzle 640 can be an internal mixing nozzle such as that shown in FIG. 4, or an external mixing nozzle such as that shown in FIG. 5. Preferably, nozzle 640 is an internal mixing nozzle.

In the embodiment shown in FIG. 6, a nitrogen gas stream 642 is input to nozzle 640 to atomize the combination flowing out of static mixer 630. As discussed above with respect to FIGS. 4 and 5, nitrogen gas stream 642 can be a single gas stream, or divided into a plurality of gas streams, to impinge upon the liquid combination to atomize it into droplets. As would be readily apparent to one skilled in the art, other gases could be used to atomize the liquid combination into droplets, and the present invention is not limited to the use of nitrogen as the atomizing gas stream.

The atomized droplets from nozzle 640 are dried in spray dryer 650. Nitrogen from a nitrogen gas supply 652 is heated by a heater 654 and input to spray dryer 650. A flow meter 656 and a temperature measurement point 658 are used to monitor the flow and temperature of the nitrogen gas input to spray dryer 650. As would be readily apparent to one skilled in the art, other drying gases could be used in spray dryer 650, such as, but not limited to, air, argon, carbon dioxide, helium, and combinations or mixtures thereof. In an alternate embodiment of the present invention, the drying gas input to spray dryer 650 is the same input used to atomize the liquid combination in nozzle 640. A mixture of gas and dried particles or powder exits from spray dryer 650 at an outlet 659. A flow conditioner 660 and temperature measurement point 662 are used to condition and monitor the characteristics of the gas-powder mixture exiting spray dryer 650. A flow conditioner suitable for use with the present invention is made by Vortab, San Marcos, Calif.

Flow conditioner 660 conditions the gas-powder mixture exiting spray dryer 650 so that the particles contained in the gas stream can be characterized by measuring the geometric diameter and the aerodynamic diameter of the particles. Flow conditioner 660 provides a more homogeneous powder distribution in the piping by imparting turbulent conditions to the gaseous stream. The more homogeneous powder distribution prevents selective or skewed sampling in the downstream sizers. After conditioning by flow conditioner 660, a sample of the gas-powder mixture flows through a geometric sizer 670 and an aerodynamic sizer 672, the operation of which will be discussed in more detail below. The sample of the gas-powder mixture is used to determine geometric and aerodynamic size. After sizing, the sample is deposited on a filter (not shown) for later disposal. The bulk of the gas-powder mixture flows directly out of flow conditioner 660 and the dry particles are collected on a bag filter 680 that retains the dry particle product while allowing the gas to pass through to an exhaust 684 and for solvent stripping. The dry particle product is removed from bag filter 680, such as by running a back pulse of nitrogen across bag filter 680, and is collected in a product collection vessel 682.

Geometric sizer 670 preferably measures volume median geometric diameter (VMGD) of the particles. An exemplary geometric sizer is the Insitec online particle sizer, available from Malvern Instruments Ltd. The Insitec device consists of an optical sensor head, a signal processing unit, and a computer for instrument control and data collection and analysis. Aerodynamic sizer 672 preferably measures mass median aerodynamic diameter (MMAD) of the particles. An exemplary aerodynamic sizer is the PS Model 3321, available from TSI, Inc., St. Paul, Minn. In one embodiment of the present invention, a computer 674 is coupled to geometric sizer 670 and to aerodynamic sizer 672. Computer 674 is used to carry out the optimization process of the present invention, described in more detail below with respect to FIG. 7. In an alternate embodiment of the present invention, a computer or processor that is part of aerodynamic sizer 672 or geometric sizer 670 is used to carry out the optimization process of the present invention.

Conventional optimization of a spray drying process is a time consuming and material intensive process, requiring the manipulation of multiple process variables, such as inlet temperature, outlet temperature, atomizer speed, drum pressure, gas flow rate, and liquid feed rate, and multiple product formulations. A typical optimization run would involve selecting a formulation and a set of process conditions, spraying the material under the selected conditions, collecting the finished dry particle powder, and characterizing the dry particles using various in vitro techniques, such as laser diffraction techniques (HELOS diffractometer and a RODOS disperser) to measure geometric diameter, an aerosizer to measure aerodynamic diameter, an ACI to measure size distribution, and measurement of tap density. Once the results of the characterization tests were complete, then the process parameters could be adjusted to optimize the characteristics of the particles. Approximately 2–3 g of material, and about two hours, are required for each such optimization run. To completely optimize process conditions to obtain final desired powder characteristics, hundreds of runs may be required. Thus, conventional optimization of the spray drying process is inefficient, time consuming, and expensive.

The system and method of the present invention significantly decreases the time and material required to optimize the spray drying process. Using the system and method of the present invention, an operator can evaluate particle characteristics in real time during the spray drying process without having to run the traditional in vitro characterization assays after the fact. Using the system and method of the present invention, process conditions can be modified in real time to optimize particle size to produce particles having a desired geometric and/or aerodynamic diameter.

Geometric sizer 670 can be used to measure the geometric diameter of the particles, and aerodynamic sizer 672 can be used to measure the aerodynamic diameter of the particles. However, in order for the aerodynamic measurement to be made, the density of the particles must be known prior to the measurement. Density ($\rho$), geometric diameter ($d_g$), and aerodynamic diameter ($d_a$) are related by the following equation: $d_a = d_g \sqrt{\rho}$. The process of the present invention uses density as the optimization variable to achieve particles having the desired aerodynamic and/or geometric diameters.

Figure 7:
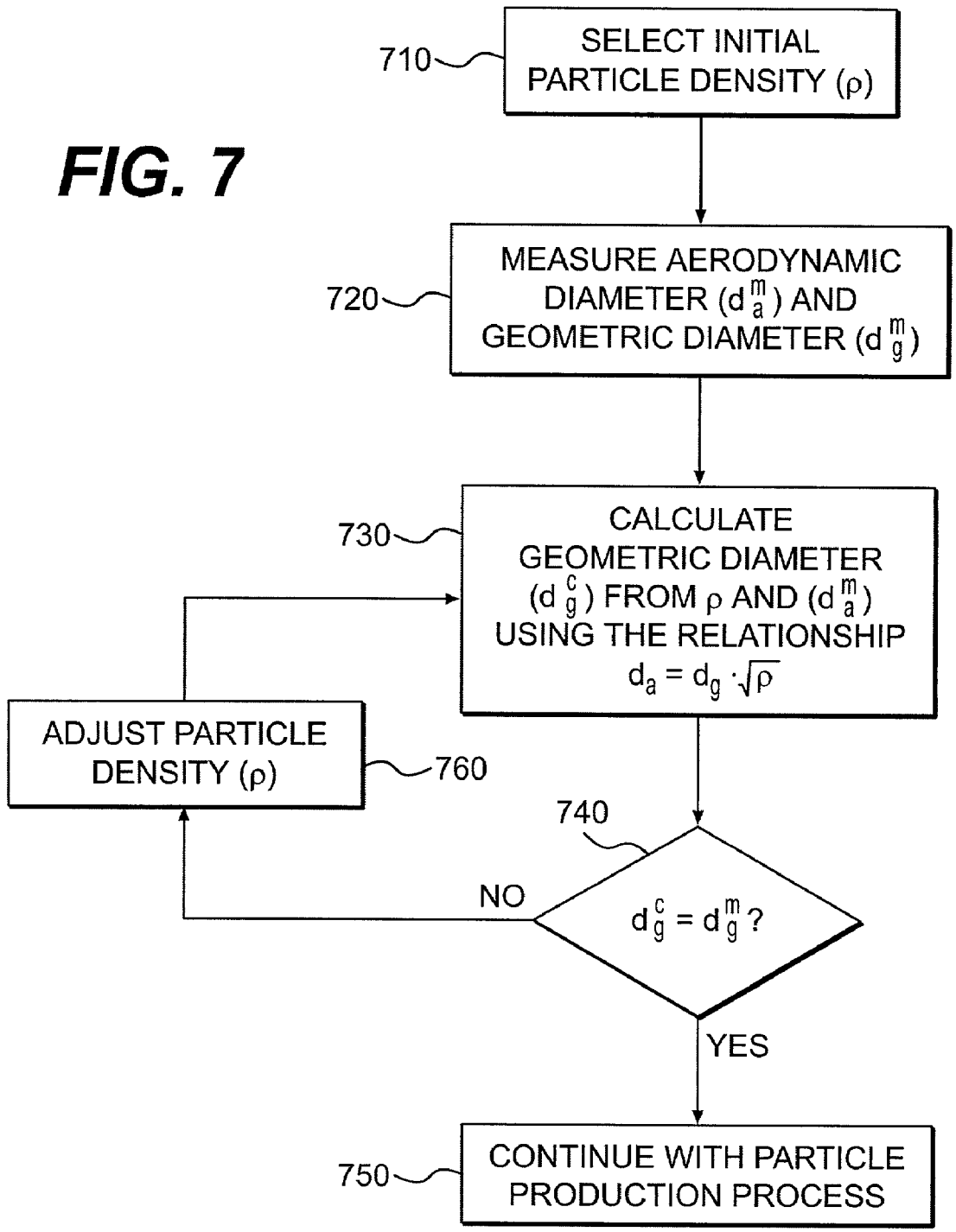
FIG. 7 shows a flow chart of one embodiment of a process of the present invention for optimizing particle size.

One embodiment of a process of the present invention for optimizing particle size is illustrated in FIG. 7. In a step 710, an initial particle density is selected, and provided to aerodynamic sizer 672. In a preferred embodiment of the present invention for preparation of dry particles suitable for inhalation into the lung, preferably into the deep lung, an initial particle density of 0.06 g/cm$^3$ is used. It should be apparent to one skilled in the art that other initial particle densities can be selected, depending upon the particular particle to be produced. In a step 720, a measured aerodynamic diameter ($d_a^m$) and a measured geometric diameter ($d_g^m$) are obtained using aerodynamic sizer 672 and geometric sizer 670, respectively. In a step 730, a calculated geometric diameter ($d_g^c$) is calculated from the initial particle density and the measured aerodynamic diameter using the equation $$d_a^m = d_g^c \sqrt{\rho}$$

If the estimated initial particle density (e.g., 0.06 g/cm$^3$) was correct for the particles being produced, then the calculated geometric diameter should be substantially equal to the measured geometric diameter measured by geometric sizer 670. If the calculated geometric diameter and the measured geometric diameter do not match, then a new density is input into aerodynamic sizer 672 and processing returns to step 730 to re-calculate geometric diameter. This process continues until the calculated geometric diameter and the measured geometric diameter match. This iterative process is illustrated in FIG. 7. In a step 740, it is determined whether $d_g^c = d_g^m$. The calculated geometric diameter is compared to the measured geometric diameter to determine a differential. If there is a differential, then, in a step 760, the particle density is adjusted, and processing returns to step 730 to again calculate geometric diameter using the adjusted value for particle density. Increasing the density decreases the geometric diameter. Decreasing the density increases the geometric diameter. The geometric diameter is again calculated in step 730, and compared to the measured geometric diameter in step 740. This process repeats until in step 740 it is determined that the calculated geometric diameter is substantially equal to the measured geometric diameter, at which point the particle production process continues, as shown in a step 750.

When using the process of the present invention as shown in FIG. 7, solutions are spray dried to form dry particles, and the aerodynamic and geometric diameters are measured. Process conditions (flow rates, temperatures, etc.) are held constant during the measurement of the aerodynamic and geometric diameters. Once the measurements are made, solvents can then be run through the spray drying system while the density iteration is calculated (steps 730, 740, and 760 in FIG. 7). This represents a significant savings of costly material, such as the aqueous solution containing active agent.

In one embodiment of the present invention, the density iteration is done with aerodynamic diameter as a fixed variable. In such an embodiment, the density is changed until the calculated geometric diameter is substantially equal to the measured geometric diameter. Once the density iteration is complete, then the density, aerodynamic diameter, and geometric diameter of the particles are known. At that point, process conditions (gas and/or liquid flow rates, temperatures, process solutions) can be changed to achieve a different density, aerodynamic, or geometric diameter. Alternatively, a process condition or process solution can be modified to determine its affect on density, aerodynamic diameter and geometric diameter.

In another embodiment of the present invention, the density iteration is done with geometric diameter as a fixed variable. In such an embodiment, process conditions, such as gas flow rate, are adjusted to achieve a desired measured geometric diameter. Aerodynamic diameter is measured. Density is then changed until the calculated geometric diameter is substantially equal to the measured geometric diameter. Once the density iteration is complete, then the density, aerodynamic diameter, and geometric diameter of the particles are known. By fixing geometric diameter in the density optimization process, particles having the same geometric diameter can be produced under different process conditions to facilitate comparisons between particles of the same geometric diameter.

Once the process reaches step 750, an operator has three values to use in decisions regarding the dry particles that have been produced to that point: geometric diameter; aerodynamic diameter; and density. One advantage of the method of the present invention is that the liquid combination from static mixer 630 needs to be atomized into spray dryer 650 for only about three minutes for the data to be collected and step 750 reached for a particular set of process conditions. In this manner, multiple sets of process conditions can be rapidly screened using a minimal amount of material. For example, once step 750 is reached, the density, geometric diameter, and aerodynamic diameter of the particles are known for a given set of process conditions and process solutions. If the desired density, geometric diameter, or aerodynamic diameter has not been achieved, then the process conditions can be modified and the density iteration process repeated. Alternatively, a particular process condition or process material can be changed, and its affect on density, aerodynamic diameter, and geometric diameter determined.

To produce dry particles that can penetrate deep into the lung, the desired geometric diameter is in the range of from about 7 to about 10 $\mu$m. Using the method and apparatus of the present invention as depicted in FIGS. 6 and 7, the density used by aerodynamic sizer 672 is adjusted to minimize particle density, while the measured geometric diameter is held constant in the 7–10 $\mu$m range. For example, dry particles containing hGH were made using the apparatus substantially as shown in FIG. 6 by selecting an initial particle density of 0.06 g/cm$^3$. The desired geometric diameter size range for reaching the deep lung is in the range of from about 7 to about 10 $\mu$m, and aerodynamic diameter size range of from about 1 to about 3 $\mu$m. The aerodynamic diameter was measured using the initial particle density of 0.06 g/cm$^3$, and the geometric diameter was measured. The geometric diameter was calculated, and compared to the measured geometric diameter. To reach the deep lung, the measured geometric diameter, and consequently the calculated geometric diameter, should be in the range of from about 7 to about 10 $\mu$m. If the calculated geometric diameter was not the same as the measured geometric diameter, the density value used in the aerodynamic sizer was reduced, and the process repeated. By minimizing particle density and holding the geometric diameter constant in the desired range, particles having the desired geometric diameter, as well as the desired low aerodynamic diameter, were produced.

Figure 9:
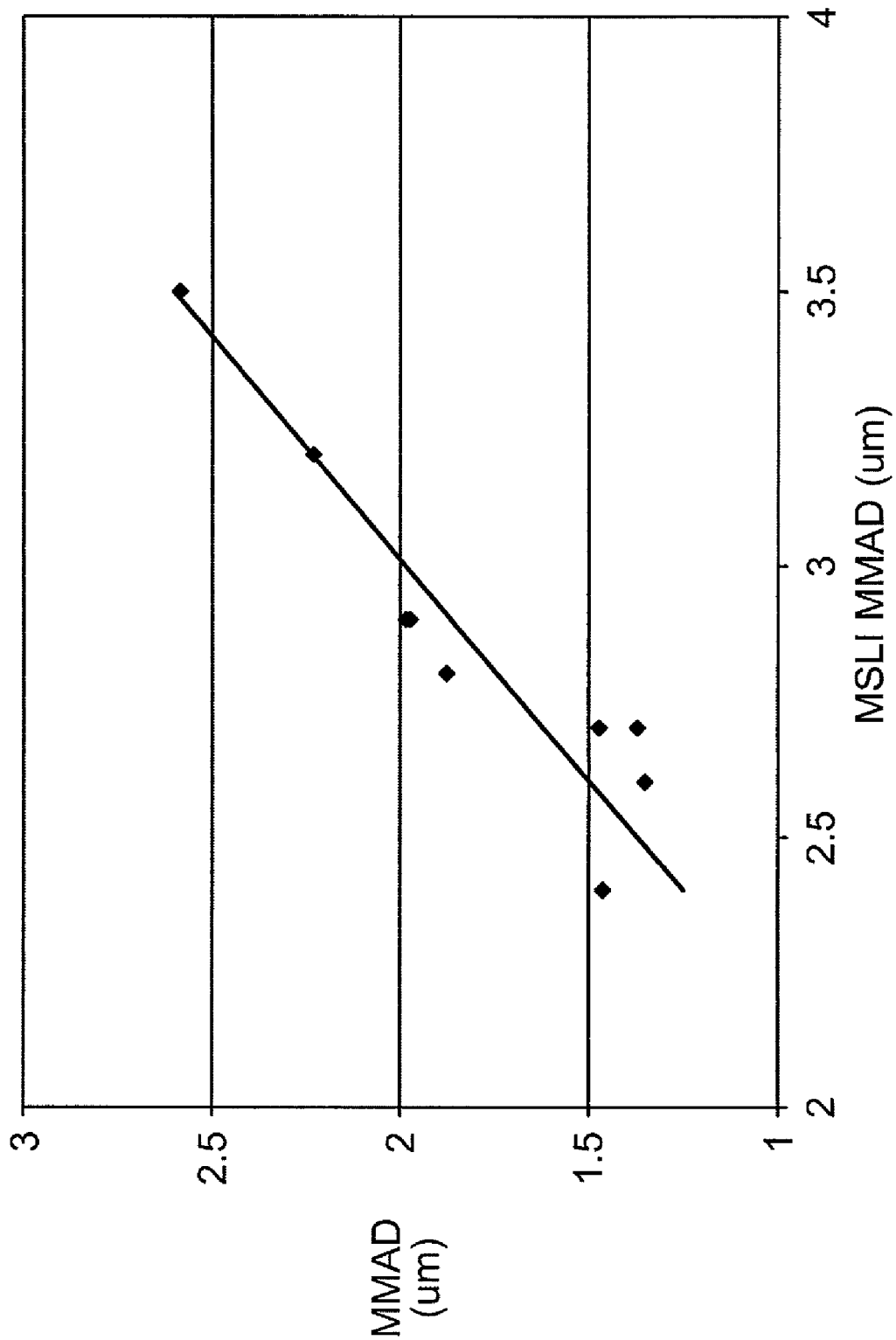
FIG. 9 shows a graph of mass median aerodynamic diameter (MMAD) as measured using the system and method of the present invention versus MMAD measured using a multi-stage liquid impinger (MSLI)

The use of density as a valid optimization variable for producing particles of the desired aerodynamic diameter is demonstrated by the graph shown in FIG. 9. FIG. 9 shows a graph of mass median aerodynamic diameter (MMAD) in $\mu$m as measured using the system and method of the present invention described above with reference to FIGS. 6 and 7, versus MMAD measured using a conventional multi-stage liquid impinger (MSLI). A MSLI works on the same basic principles as an ACI device described above. However, instead of having dry metal plates for stages like an ACI, a MSLI has liquid-containing stages. Each MSLI stage consists of an ethanol-wetted glass frit. The wetted stage is used to prevent bouncing and re-etrainment, which can occur using the ACI. The purpose of the liquid is to eliminate the presence of bounce in the system, typically leading to greater accuracy than an ACI. The MSLI used for the data illustrated in FIG. 9 included 5 stages. As can be seen from FIG. 9, the MMAD measured using the density iteration process of the present invention (y-axis) correlated well with the MMAD measured using an MSLI (x-axis), with the MMAD measured using the density iteration process being a reliable predictor of trends in MMAD measured using the MSLI.

Figure 8:
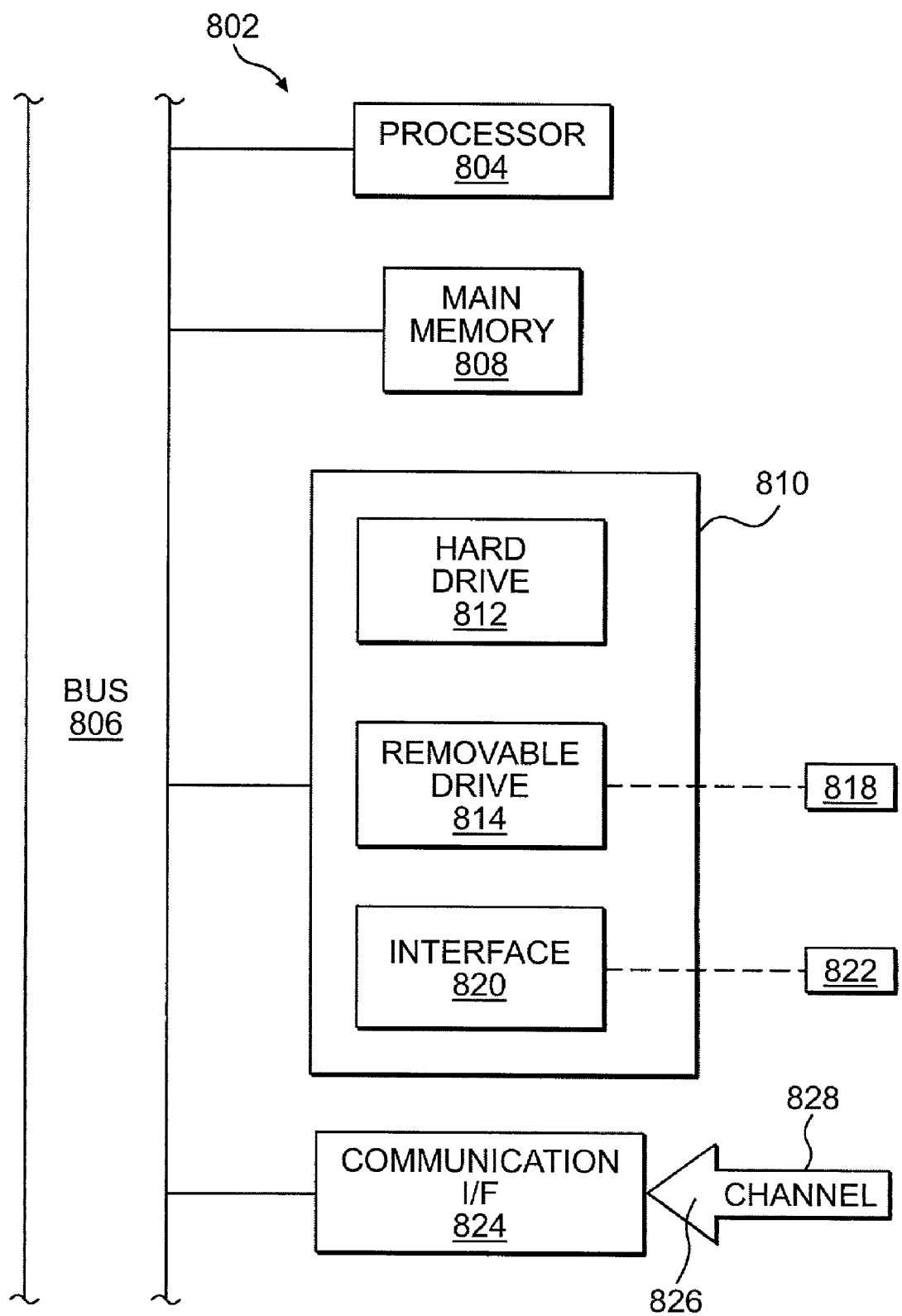
FIG. 8 illustrates one embodiment of a computer system suitable for use with the present invention.

As noted above with respect to FIGS. 6 and 7, a computer or computer system can be used to control the aerodynamic and/or geometric particle sizers, and to carry out the particle size optimization process. An exemplary computer system suitable for use with the present invention is shown in FIG. 8. The computer system 802 includes one or more processors, such as a processor 804. The processor 804 is connected to a communication bus 806. After reading this description, it will become apparent to a person skilled in the relevant art how to implement the invention using other computer systems and/or computer architectures.

The computer system 802 also includes a main memory 808, preferably random access memory (RAM), and can also include a secondary memory 810. The secondary memory 810 can include, for example, a hard disk drive 812 and/or a removable storage drive 814, representing a floppy disk drive, a magnetic tape drive, an optical disk drive, etc.

The removable storage drive 814 reads from and/or writes to a removable storage unit 818 in a well-known manner. The removable storage unit 818, represents a floppy disk, magnetic tape, optical disk, etc. which is read by and written to by the removable storage drive 814. As will be appreciated, the removable storage unit 818 includes a computer usable storage medium having stored therein computer software and/or data.

In alternative embodiments, the secondary memory 810 may include other similar means for allowing computer programs or other instructions to be loaded into the computer system 802. Such means can include, for example, a removable storage unit 822 and an interface 820. Examples of such can include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 822 to the computer system 802.

The computer system 802 can also include a communications interface 824. The communications interface 824 allows software and data to be transferred between the computer system 802 and external devices. Examples of the communications interface 824 can include a modem, a network interface (such as an Ethernet card), a communications port, a PCMCIA slot and card, etc. Software and data transferred via the communications interface 824 are in the form of signals 826 that can be electronic, electromagnetic, optical or other signals capable of being received by the communications interface 824. Signals 826 are provided to communications interface via a channel 828. A channel 828 carries signals 826 and can be implemented using wire or cable, fiber optics, a phone line, a cellular phone link, an RF link and other communications channels.

In this document, the terms "computer program medium" and "computer usable medium" are used to generally refer to media such as the removable storage device 818, a hard disk installed in hard disk drive 812, and signals 826. These computer program products are means for providing software to the computer system 802.

Computer programs (also called computer control logic) are stored in the main memory 808 and/or the secondary memory 810. Computer programs can also be received via the communications interface 824. Such computer programs, when executed, enable the computer system 802 to perform the features of the present invention as discussed herein. In particular, the computer programs, when executed, enable the processor 804 to perform the features of the present invention. Accordingly, such computer programs represent controllers of the computer system 802.

In an embodiment where the invention is implemented using software, the software may be stored in a computer program product and loaded into the computer system 802 using the removable storage drive 814, the hard drive 812 or the communications interface 824. The control logic (software), when executed by the processor 804, causes the processor 804 to perform the functions of the invention as described herein.

In another embodiment, the invention is implemented primarily in hardware using, for example, hardware components such as application specific integrated circuits (ASICs). Implementation of such a hardware state machine so as to perform the functions described herein will be apparent to persons skilled in the relevant art(s). In yet another embodiment, the invention is implemented using a combination of both hardware and software.

In a preferred embodiment, the spray dried particles of the invention have a tap density less than about 0.4 g/cm³. Particles that have a tap density of less than about 0.4 g/cm³ are referred to herein as "aerodynamically light particles". More preferred are particles having a tap density less than about 0.1 g/cm³. Tap density can be measured by using instruments known to those skilled in the art such as, but not limited to, the Dual Platform Microprocessor Controlled Tap Density Tester (Vankel Technology, Cary, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopoeia convention, Rockville, Md., $10^{th}$ Supplement, 4950–4951, 1999. Features that can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm³.

Aerodynamically light particles have a preferred size, e.g., a volume median geometric diameter (VMGD) of at least about 5 μm. In one embodiment, the VMGD is from about 5 μm to about 30 μm. In another embodiment of the invention, the particles have a VMGD ranging from about 10 μm to about 30 μm. In other embodiments, the particles have a median diameter, mass median diameter (MMD), a mass median envelope diameter (MMED) or a mass median geometric diameter (MMGD) of at least 5 μm, for example from about 5 μm to about 30 μm.

The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 μm and about 5 μm. In another embodiment of the invention, the MMAD is between about 1 μm and about 3 μm. In a further embodiment, the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

Particles that have a tap density less than about 0.4 g/cm³, median diameters of at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In another embodiment of the invention, the particles have an envelope mass density, also referred to herein as "mass density" of less than about 0.4 g/cm³. Particles also having a mean diameter of between about 5 μm and about 30 μm are preferred. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm³ and a mean diameter of between about 5 μm and about 30 μm mass mean aerodynamic diameter is between about 1 μm and about 5 μm.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials* 7: 61–66 (1986); Krenis, L. J. and Strauss, B., *Proc. Soc. Exp. Med.*, 107: 748–750 (1961); and Rudt, S. and Muller, R. H., *J. Contr. Rel.*, 22: 263–272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992)), by the formula:

$$d_{aer}=d\sqrt{\rho}$$

where the envelope mass p is in units of g/cm³. Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.*, 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho} \mu m \text{ (where } \rho<1 \text{ g/cm}^3\text{)};$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology*, 58: 1–10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed.

In one embodiment of the invention, the particles include a biologically active (bioactive) compound, for example a therapeutic, prophylactic or diagnostic agent. Bioactive compounds or agents also are referred to herein as drugs, active agents, or medicaments. The amount of bioactive agent present in the particles generally ranges between about 0.1% weight and about 100% weight, preferably between about 1.0% weight and about 100% weight.

Examples of biologically active agents include synthetic inorganic and organic compounds, proteins, peptides, polypeptides, DNA and RNA nucleic acid sequences having therapeutic, prophylactic or diagnostic activities. Nucleic acid sequences include genes, antisense molecules which bind to complementary DNA or RNA and inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. Compounds with a wide range of molecular weight can be used, for example, between 100 and 500,000 grams or more per mole.

The particles can include a therapeutic agent for local delivery within the lung, such as agents for the treatment of asthma, chronic obstructive pulmonary disease (COPD), emphysema, or cystic fibrosis, or for systemic treatment. For example, genes for the treatment of diseases such as cystic fibrosis can be administered, as can beta agonists steroids, anticholinergics and leukotriene modifiers for asthma. Other specific therapeutic agents include, but are not limited to, human growth hormone, insulin, calcitonin, gonadotropin-releasing hormone, luteinizing hormone releasing hormone (LHRH), granulocyte colony-stimulating factor ("G-CSF"), parathyroid hormone and PTH-related peptide, somatostatin, testosterone, progesterone, estradiol, nicotine, fentanyl, norethisterone, clonidine, scopolamine, salicylate, cromolyn sodium, salmeterol, formeterol, albuterol, epinephrine, L-dopa, and diazepam, as well as medicaments that primarily target the central nervous system, kidneys, heart or other organs.

Diagnostic agents include but are not limited to imaging agents which include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include but are not limited to the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

The particles can include additional component(s). Such additional components may be referred to herein as excipients, and can include, for example, phospholipids, surfactants, amino acids, and polymers. In a preferred embodiment, the particles include one or more phospholipids, such as, for example, a phosphatidylcholine, phosphatidylethanolamine, phosphatidylglycerol, phosphatidylserine, phosphatidylinositol or a combination thereof. In one embodiment, the phospholipids are endogenous to the lung. Specific examples of phospholipids are shown in Table 10. Combinations of phospholipids can also be employed.

TABLE 10

| | |
|---|---|
| Dilaurylolyphosphatidylcholine (C12:0) | DLPC |
| Dimyristoylphosphatidylcholine (C14:0) | DMPC |
| Dipalmitoylphosphatidylcholine (C16:0) | DPPC |
| Distearoylphosphatidylcholine (C18:0) | DSPC |
| Dioleoylphosphatidylcholine (C18:1) | DOPC |
| Dilaurylolylphosphatidylglycerol | DLPG |
| Dimyristoylphosphatidylglycerol | DMPG |
| Dipalmitoylphosphatidylglycerol | DPPG |
| Distearoylphosphatidylglycerol | DSPG |
| Dioleoylphosphatidylglycerol | DOPG |
| Dimyristoyl phosphatidic acid | DMPA |
| Dimyristoyl phosphatidic acid | DMPA |
| Dipalmitoyl phosphatidic acid | DPPA |
| Dipalmitoyl phosphatidic acid | DPPA |
| Dimyristoyl phosphatidylethanolamine | DMPE |
| Dipalmitoyl phosphatidylethanolamine | DPPE |
| Dimyristoyl phosphatidylserine | DMPS |
| Dipalmitoyl phosphatidylserine | DPPS |
| Dipalmitoyl sphingomyelin | DPSP |
| Distearoyl sphingomyelin | DSSP |

Charged phospholipids also can be employed. Examples of charged phospholipids are described in U.S. patent application entitled "Particles for Inhalation Having Sustained Release Properties," Ser. No. 09/752,106 filed on Dec. 29, 2000, and in U.S. patent application Ser. No. 09/752,109 entitled "Particles for Inhalation Having Sustained Release Properties", filed on Dec. 29, 2000; the entire contents of both are incorporated herein by reference.

The phospholipid can be present in the particles in an amount ranging from about 5 weight percent (%) to about about 95 weight %. Preferably, it can be present in the particles in an amount ranging from about 20 weight % to about 80 weight %.

The phospholipids or combinations thereof can be selected to impart controlled release properties to the spray dried particles produced by the methods of the invention. Particles having controlled release properties and methods of modulating release of a biologically active agent are described in U.S. Provisional Patent Application No. 60/150,742 entitled "Modulation of Release From Dry Powder Formulations by Controlling Matrix Transition," filed on Aug. 25, 1999 and U.S. Non-Provisional patent application Ser. No. 09/644,736, filed on Aug. 23, 2000, with the title "Modulation of Release From Dry Powder Formulations". The contents of both are incorporated herein by reference in their entirety.

In another embodiment of the invention particles include a surfactant. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

In addition to lung surfactants, such as, for example, the phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85), Tween 20 or Tween 80 (Polyoxyethylene Sorbitan Monooleate); and tyloxapol.

The surfactant can be present in the particles in an amount ranging from about 0.01 weight % to about 5 weight %. Preferably, it can be present in the particles in an amount ranging from about 0.1 weight % to about 1.0 weight %.

Methods of preparing and administering particles including surfactants, and, in particular phospholipids, are disclosed in U.S. Pat. No. 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety.

In another embodiment of the invention, the particles include an amino acid. Hydrophobic amino acids are preferred. Suitable amino acids include naturally occurring and non-naturally occurring hydrophobic amino acids. Examples of amino acids which can be employed include, but are not limited to: glycine, proline, alanine, cysteine, methionine, valine, leucine, tyrosine, isoleucine, phenylalanine, tryptophan. Preferred hydrophobic amino acids, include but not limited to, leucine, isoleucine, alanine, valine, phenylalanine, glycine and tryptophan. Amino acids which include combinations of hydrophobic amino acids can also be employed. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1–C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F)—O (aliphatic, substituted aliphatic, benzyl, substituted benzyl, aryl or substituted aryl group), —CN, —$NO_2$, —COOH, —$NH_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —$CONH_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—$NH_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acid analogs and salts thereof can be obtained commercially. Others can be synthesized by methods known in the art. Synthetic techniques are described, for example, in Green and Wuts, *"Protecting Groups in Organic Synthesis"*, John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids and one or more phospholipids or surfactants can also be employed.

The amino acid can be present in the particles in an amount from about 0 weight % to about 60 weight %. Preferably, the amino acid can be present in the particles in an amount ranging from about 5 weight % to about 30 weight %. The salt of a hydrophobic amino acid can be present in the liquid feed in an amount from about 0 weight % to about 60 weight %. Preferably, the amino acid salt is present in the liquid feed in an amount ranging from about 5 weight % to about 30 weight %. Methods of forming and delivering particles which include an amino acid are described in U.S. patent application Ser. No. 09/382,959, filed on Aug. 25, 1999, entitled "Use of Simple Amino Acids to Form Porous Particles During Spray Drying" and in U.S. patent application Ser. No. 09/644,320 filed on Aug. 23, 2000, entitled "Use of Simple Amino Acids to Form Porous Particles"; the teachings of both are incorporated herein by reference in their entirety.

In another embodiment of the invention, the particles include a carboxylate moiety and a multivalent metal salt. One or more phospholipids also can be included. Such compositions are described in U.S. Provisional Application No. 60/150,662, filed on Aug. 25, 1999, entitled "Formulation for Spray-Drying Large Porous Particles," and U.S. patent application Ser. No. 09/644,105 filed on Aug. 23, 2000, entitled "Formulation for Spray-Drying Large Porous Particles"; the teachings of both are incorporated herein by reference in their entirety. In a preferred embodiment, the particles include sodium citrate and calcium chloride.

Biocompatible, and preferably biodegradable polymers also can be included in the particles. Particles including such polymeric materials are described in U.S. Pat. No. 5,874,064, issued on Feb. 23, 1999 to Edwards et al., the teachings of which are incorporated herein by reference in their entirety, and in U.S. Pat. No. 6,136,295, issued on Oct. 24, 2000 to Edwards et al., the entire teachings of which are incorporated herein by reference.

The particles can also include a material such as, for example, dextran, polysaccharides, lactose, trehalose, cyclodextrins, proteins, peptides, polypeptides, fatty acids, inorganic compounds, phosphates.

The total concentration of solids in the liquid feed from which the particles are formed ranges from about 0.1% to about 0.5% and higher. Solids can include biologically active agent, excipient, phospholipid, surfactants, salts, buffers, metals, and other compounds.

Particles produced by the methods of the invention and which include a medicament, for example one or more of the bioactive agents described above, can be administered to the respiratory tract of a patient in need of treatment, prophylaxis or diagnosis. Administration of particles to the respiratory system can be by means known in the art. For example, particles are delivered from an inhalation device. In a preferred embodiment, particles are administered via a dry powder inhaler (DPI). Metered-dose-inhalers (MDI), or instillation techniques, also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848 issued Dec. 7, 1999 to Patton, et al. Other examples of suitable inhalers include, but are not limited to, the Spinhaler® (Fisons, Loughborough, U.K.), Rotahaler® (Glaxo-Wellcome, Research Triangle Technology Park, N.C.), FlowCaps® (Hovione, Loures, Portugal), Inhalator® (Boehringer-Ingelheim, Germany), and the Aerolizer® (Novartis, Switzerland), the Diskhaler® (Glaxo-Wellcome, RTP, N.C.) and others known to those skilled in the art.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung. In another embodiment of the invention, delivery is primarily to the central airways. Delivery to the upper airways can also be obtained.

In one embodiment of the invention, delivery to the pulmonary system of particles is in a single, breath-actuated step, as described in U.S. Non-Provisional Patent Application, "High Efficient Delivery of a Large Therapeutic Mass Aerosol", application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

As used herein, the term "effective amount" means the amount needed to achieve the desired therapeutic or diagnostic effect or efficacy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). In one example, effective amounts of albuterol sulfate range from about 100 micrograms (μg) to about 1.0 milligram (mg).

Aerosol dosage, formulations and delivery systems also may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6: 273–313, 1990; and in Moren, "Aerosol dosage forms and formulations," in: *Aerosols in Medicine. Principles, Diagnosis and Therapy*, Moren, et al., Eds, Esevier, Amsterdam, 1985.

The particles of the invention can be employed in compositions suitable for drug delivery to the pulmonary system. For example, such compositions can include the particles and a pharmaceutically acceptable carrier for administration to a patient, preferably for administration via inhalation. The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass median diameters for example in the range between about 50 μm and about 100 μm.

The present invention will be further understood by reference to the following non-limiting examples.

EXAMPLES

Preparation of Dry Particles Containing hGH

In a preferred aspect of the present invention, it was desired to prepare inhalable dry particles containing hGH (human growth hormone) that would maximize the amount of active hGH that reached the alveolar space. To do so, it was determined that the inhalable dry particles should have a FPF(5.6) of at least about 85% and a FPF(3.4) of at least about 55%. It was also desired to have at least 95% of the hGH in the dry particles be "readily extractable", that is, soluble in buffer solution. When the hGH is exposed to incompatible components, for example, organic solutions such as ethanol solution, the hGH degrades or denatures, resulting in degradation products that include insoluble aggregates and soluble dimer. The method and apparatus of the present invention were developed to minimize the amount of insoluble aggregates and soluble dimer in the finished dry particles by minimizing the contact between the hGH solution and the incompatible ethanol solution by combining them rapidly in a static mixer.

The following examples illustrate preparation of inhalable dry particles containing hGH. Unless indicated otherwise, bulk raw hGH was supplied by Eli Lilly, Inc. as lyophilized powder. 1,2 Dipalmitoyl-sn-Glycero-3-Phosphocholine (DPPC) was obtained from Avanti Polar Lipids. USP grade 200 proof ethyl alcohol and USP (United States Pharmacopeia) Sterile Water for Irrigation were used.

56.1 wt % hGH/40.6 wt % DPPC/3.3 wt % Sodium Phosphate

The dry particles were prepared in accordance with the following procedure, using equipment substantially the same as that illustrated in FIG. 2. The lyophilized hGH powder was allowed to warm to room temperature for at least ½ hour. The hGH was dissolved in 1.7 mM sodium phosphate buffer (pH 7.4) to form a concentrated hGH solution. The pH of the hGH concentrate was increased to 7.4 using 1.0 N NaOH. The hGH concentrate was passed through a Millipore 0.22 μm Opticap filter. The concentration of the hGH concentrate was determined using a Beckman Du® 640 spectrophotometer. The hGH concentrate solution was diluted with 1.7 mM sodium phosphate buffer (pH 7.4) to achieve an hGH concentration of 3.57 g/Kg. The resulting aqueous solution was transferred to a sealed vessel, such as feed vessel 210. The organic solution was prepared by dissolving the DPPC in 200 proof ethyl alcohol to a concentration of 1.40 g/Kg. The organic solution was transferred into a sealed vessel, such as feed vessel 220.

The aqueous phase was pumped at 15 ml/min±3 ml/min, and the organic phase was pumped at 35 ml/min±3 ml/min into a twelve inch long static mixer, such as static mixer 230. The combination liquid flowed from the static mixer into a rotary atomizer (such as atomizer 240) using a 24 vaned rotary atomizer wheel (Niro) operating at 34,500 rpm±2000 rpm. The combination was atomized into small droplets, which entered the Niro Size 1 spray dryer (such as spray dryer 250) utilizing dry nitrogen gas flowing at 105 Kg/hr±4 Kg/hr. The inlet temperature of the spray dryer was maintained at 88° C.±5° C. such that the outlet temperature fell within the range of 45° C.±2° C. The particles were collected in a bag house, such as bag house 260. The resulting dry particles had a mean MMAD of 2.52 μm and a mean VMGD of 10.20 μm.

Size-exclusion HPLC was used to detect and quantitate aggregate formation in the resulting dry particles. As described in more detail below, samples were dissolved in 25 mM phosphate buffer, pH 7.0, and in 67% 25 mM phosphate buffer, pH 7.0, containing 33% n-propanol, and filtered through 0.45 μm syringe filters prior to chromatography. Using this technique, hGH elutes as monomer (main peak) at a retention time of 12 to 17 minutes. The appearance of a leading shoulder on the monomer main peak indicates the presence of soluble dimer. The amount of soluble dimer and soluble monomer can be obtained by determining their respective peak areas. The amount of insoluble aggregate is calculated from the following formula:

$$\text{Insoluble Aggregate } (\%)=(1-A/B\times\text{Area Correction})\times 100\%$$

A=Monomer Peak Area of hGH dry particles dissolved in 25 mM phosphate buffer.

B=Monomer Peak Area of hGH dry particles dissolved in 67% 25 MM phosphate buffer, pH 7.0 containing 33% n-propanol.

Area Correction=1.027 (accounts for the difference of the hGH standard peak area between injections from 33% n-propanol and buffer).

Size exclusion HPLC was carried out using a Waters 2690 HPLC system operating in isocratic mode with a Waters 2487 UV Detector and a Tosohas TSK G3000SW, 10 μm (7.5 mm×300 mm) column. The size exclusion column was run at 0.6 ml/min using a 0.063 M phosphate buffer: isopropyl alcohol (97:3) mobile phase, at pH 7.0. UV detection was at 214 nm.

An alternative method for determining soluble and insoluble aggregates in protein such as hGH is described below. This method is performed using size exclusion HPLC with detection at 214 nm on a Waters 2690 system with a Waters 2486 dual wavelength detector. A TSK GEL 3000SW 7.5 mm×300 mm column is used for the separation with a 63 mM potassium phosphate, pH 7.0 containing 3% IPA mobile phase flowing at 0.6 mL/min for 30 min/run at room temperature. Manual integration is performed to quantify monomer, high molecular weight protein (soluble aggregates) and acid dissolved hGH (insoluble aggregates) areas versus a hGH reference standard calibration curve.

The procedure is as follows:

Weigh 20 mg of hGH into a scintillation vial and transfer in 20 ml of diluent (25 mM potassium phosphate). This is approximately 0.8 mg/mL hGH monomer.

Gently disperse powder solution.

Remove approximately 3 ml and filter into an HPLC vial and inject 20 µL onto the SE HPLC column. This solution is used to determine the hGH monomer content and the amount of high molecular weight protein (soluble aggregates).

Remove a further 1 ml and transfer to a centrifuge tube. (Perform in duplicate.)

Centrifuge for 10 minutes at 14,000 rpm. Remove and discard the supernatant.

Wash the pellet to remove soluble hGH with 1 ml of water, and centrifuge for 10 minutes. Repeat this three times.

Following the third washing and removal of the water, centrifuge the tubes one more time to remove any remaining water. Do not disrupt the pellet.

Reconstitute the pellet with 1 ml of 0.01N HCl, and allow it to dissolve for 15 minutes.

Transfer the solution to a HPLC vial and inject 100 µL onto the column.

The buffer soluble hGH content is determined from the injection of the first solution. The insoluble hGH content is determined from injection of the second solution in 0.01N HCl. The percent readily extractable hGH is calculated as buffer soluble hGH divided by total hGH content (soluble plus insoluble hGH).

Three experimental runs were made to determine the effect of time in the incompatible ethanol solution on the integrity of the hGH protein. For two of the experiments, a static mixer was not used. Rather, the aqueous and organic solutions were combined, and the combination was maintained for a period of time prior to atomization and spray drying. In the first experiment (sample 2 in Table 11 below), the aqueous and the organic solutions were combined prior to spraying, such that the final volume was 1.25 L, and the resulting combination was spray dried over a period of 25 minutes. In the second experiment (sample 1 in Table 11 below), the aqueous and organic solutions were combined prior to spraying, such that the final volume was 28 L, and the resulting combination was spray dried over a period of 8 hours (560 minutes). In the third experiment, (sample 3 in Table 11 below), the static mixer was used so that the exposure of the hGH to ethanol was about 6 seconds (0.1 minute). The total batch size for sample 3 was 0.375 L of the aqueous solution and 0.875 L of the ethanol solution.

TABLE 11

| Sample | Static Mixer | Maximum Exposure Time (minutes) | Soluble Aggregate | Insoluble Aggregate |
|---|---|---|---|---|
| 1 | No | 560 | 1.60% | 26% |
| 2 | No | 25 | 5.40% | 14% |
| 3 | Yes | 0.1 | 3.90% | 9% |

All of the samples in Table 11 were prepared under the same conditions, with the exception of the amount of exposure time between the aqueous and ethanol solutions prior to spray drying. As can be seen from the results in Table 11, the insoluble aggregate of the hGH monomer increased as a function of exposure time to 70% (v/v) ethanol solution. Use of the static mixer decreased the insoluble aggregates by about 17%.

93.5 wt % hGH/6.5 wt % Sodium Phosphate: 10 g/L Ammonium Bicarbonate; 12 g/L Solids Lipid-free particles with a formulation containing hGH and sodium phosphate monohydrate were prepared as follows using apparatus substantially as shown in FIG. 6. The aqueous solution was prepared by preparing a bulk sodium phosphate solution at 100 mM at pH 7.4 and a bulk ammonium bicarbonate solution at 50 g/L. 52 mL of 100 mM sodium phosphate buffer at pH 7.4 was added to 268 mL of water for irrigation. To this was added 200 mL of the 50 g/L ammonium bicarbonate solution and 200 mL of ethanol. The resulting solution was combined in a static mixer with 280 mL of bulk hGH at 40 g/L in 1.7 mM sodium phosphate buffer at pH=7.4. Solute concentration in the combined solution was 12 g/L. The combined solution was spray dried under the following process conditions:

Inlet temperature~74° C.

Outlet temperature from the drying drum~40° C.

Nitrogen drying gas=110 kg/hr

Nitrogen atomization gas=64 g/min

2 Fluid internal mixing nozzle atomizer

Nitrogen atomization pressure~90 psi

Liquid feed rate=25 ml/min

Liquid feed temperature~22° C.

Pressure in drying chamber=−2.0 in water

The resulting particles had a FPF(5.6) of 75%, and a FPF(3.4) of 70%, both measured using a 2-stage ACI. The volume mean geometric diameter was 8 μm at 1.0 bar. The resulting particles had a soluble dimer fraction of 1.2% and a readily extractable hGH fraction of 97.5%.

The combination solution flowing out of the static mixer was fed into a two-fluid nozzle atomizer located above the spray dryer, such as atomizer 640. The contact between the atomized droplets from the atomizer and the heated nitrogen caused the liquid to evaporate from the droplets, resulting in dry porous particles. The resulting gas-solid stream was fed to bag filter 680 that retained the resulting dry particles, and allowed the hot gas stream containing the drying gas (nitrogen), evaporated water, and ethanol to pass. The dry particles were collected into product collection vessel 682.

In order to obtain dry particles of particular physical and chemical characteristics, in vitro characterization tests can be carried out on the finished dry particles, and the process parameters adjusted accordingly, as would be apparent to one skilled in the art. Particles produced using the apparatus shown in FIG. 2 had a VMGD of 8.4 μm, FPF(5.6) of 89% to 93%, readily extractable hGH fraction of 95.5%, and a soluble dimer fraction of 3%. Particles containing 93.5 wt % hGH and 6.5 wt % sodium phosphate were produced using the apparatus substantially as shown in FIG. 6. In this manner, the desired aerodynamic diameter, geometric diameter, and particle density could be obtained for these particles in real-time, during the production process.

80 wt % hGH/14 wt % DPPC/6 wt % Sodium Phosphate; 15 g/L Ammonium Bicarbonate; 6 g/L Solids Particles with a formulation containing hGH, DPPC, and sodium phosphate were prepared as follows using apparatus substantially as shown in FIG. 6. The aqueous solution was prepared by preparing a bulk sodium phosphate solution at pH 7.4 and a bulk ammonium bicarbonate solution. 280 mg of sodium phosphate monobasic was added to 457 mL of water for irrigation. The pH was adjusted to 7.4 using 1.0 N NaOH. To this was added 15 g of ammonium bicarbonate and 200 mL of ethanol. 343 mL of 14 g/L hGH bulk solution (4.8 g of hGH in 1.7 mM sodium phosphate buffer at pH 7.4) was added to complete the aqueous solution. 840 mg of DPPC was added to 200 mL of ethanol to form the ethanol solution. The aqueous solution was combined in a static mixer with the ethanol solution using a flow rate of 24 mL/min for the aqueous solution and a flow rate of 6 mL/min for the ethanol solution. Solute concentration in the combined solution was 6 g/L. The combined solution was spray dried under the following conditions:

Inlet temperature~120° C.

Outlet temperature from the drying drum~70° C.

Nitrogen drying gas=110 kg/hr.

Nitrogen atomization gas=40 g/min.

2 fluid internal mixing nozzle atomizer.

Nitrogen atomization pressure~65 psi.

Liquid feed rate=30 mL/min (24 mL/min aqueous and 6 mL/min ethanol).

Liquid feed temperature~22° C.

Pressure in drying chamber=−2.0 in water.

The resulting particles had a FPF (5.6) of 89%, and a FPF (3.4) of 76%, both measured using a 2-stage ACI. The volume mean geometric diameter was 7.4 μm at 1.0 bar. The resulting particles had a soluble dimer fraction of 3.5% and a readily extractable hGH fraction of 95.6%.

Through the process of the present invention, the formation of protein aggregates can be minimized. Reduced protein aggregation is achieved through the use of the static mixer, and by controlling the level of ethanol in the ethanol solution.

Figure 10:
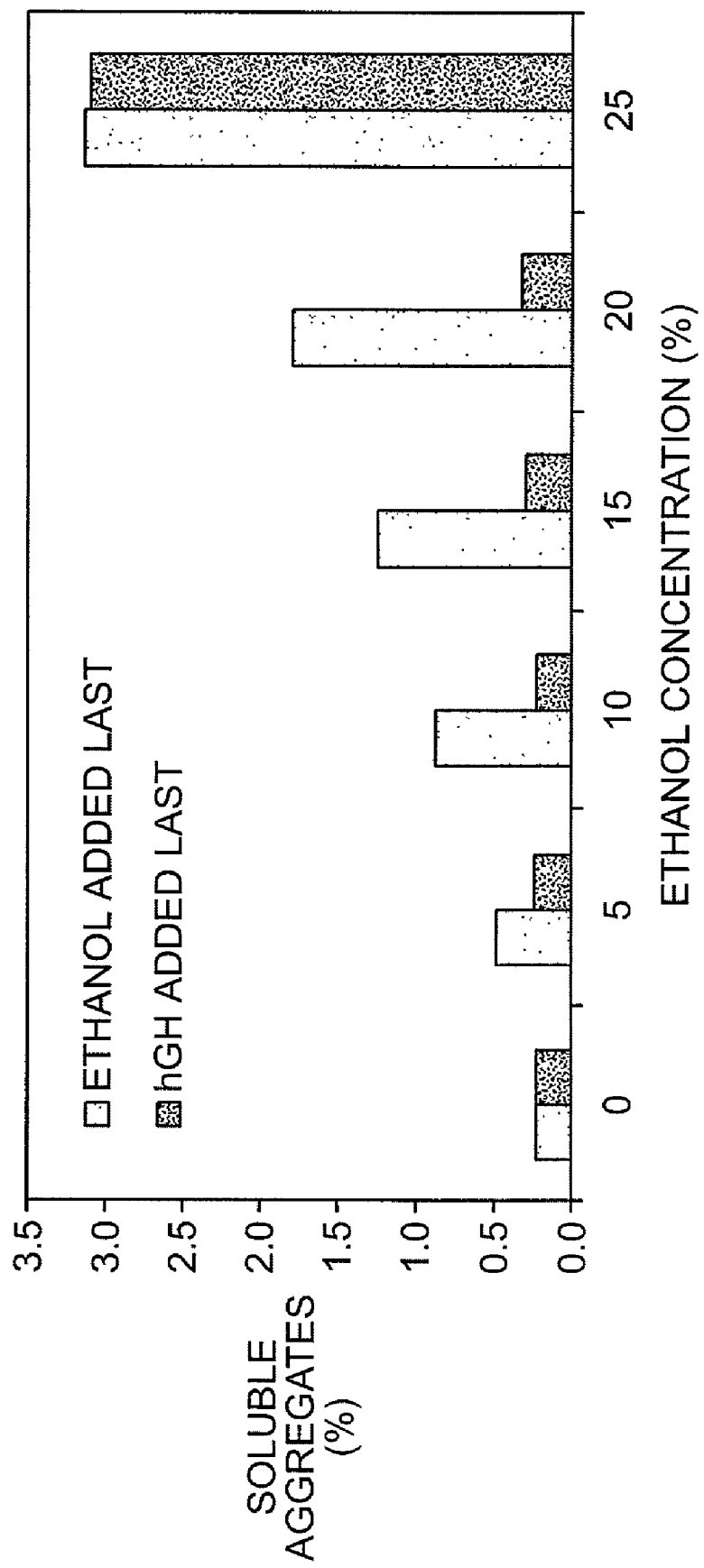
FIG. 10 shows a graph that illustrates the effect of the order of addition on soluble aggregate (dimer) levels as a function of ethanol concentration.

A comparison of powders produced with either batch or static mixing is shown below in Table 12. All of the lots were produced using substantially the same process materials, and process conditions. The five combined lots produced with batch mixing generate a lower level of high molecular weight (HMW) protein (soluble dimer=HMW protein) than is generated using a static mixing process (n=4 lots). Batch mixing of the spray-dry solution containing 20% ethanol appears beneficial, as it might allow time to disrupt hydrophobic interactions between the hGH molecules, and thus reduce hGH aggregation. When ethanol is added to the diluted hGH aqueous phase via the static mixer, a prolonged ethanol-aqueous interface occurs and this results in powders having somewhat higher levels of soluble aggregates. This occurs because the hGH in the aqueous phase is exposed to higher than optimal ethanol levels which can cause the hGH to unfold and denature. If a static mixer is used for the mixing process, then the hGH is preferably added as a concentrate to a diluted ethanol/aqueous phase. This is equivalent to adding the hGH last in batch mixing. This is preferred because it eliminates exposing the hGH to high ethanol levels which can perturb its protein structure. The effect of the order of addition on soluble aggregate (dimer) levels as a function of ethanol concentration is shown in FIG. 10. The soluble aggregates level is reduced by adding the hGH last (right column), until the ethanol concentration exceeds about 20%.

TABLE 12

| Lots N = | hGH Monomer | HMW Protein | Insoluble Aggregates | Mixing |
|---|---|---|---|---|
| 5 | 79.6% | 3.3% | 4.4% | batch |
| 4 | 78.4% | 5.0% | 5.9% | static |

Conversely, at higher levels of ethanol (>20%), destabilization of the protein structure may occur, and static mixing was demonstrated to be a better method of mixing because it reduces the time of exposure of the hGH to the ethanol phase (Table 13). This results in powders with lower levels of insoluble aggregates. It has been demonstrated (data not shown) that the time of exposure of the hGH to the ethanol can affect the level of soluble aggregate formed in the spray-drying formulation solution.

TABLE 13

| Lot Number | HMW Protein | Insoluble Aggregates | Organic, Excipient, Mixing |
|---|---|---|---|
| 3-63063 | 5.4% | 14.0% | 70%, EtOH, batch |
| 3-10697 | 3.9% | 9.0% | 70%, EtOH, static |

The addition of non-ionic surfactants to solutions containing hGH significantly reduces the formation of insoluble aggregates during exposure to an air/liquid interface. Non-ionic surfactants, such as Tween, preferentially adsorb to air-water interfaces and stabilize proteins against aggregate during processing, such as spray drying. However, use of non-ionic surfactants such as Tween is not preferred in pulmonary products due to potential toxic effects. However, in accordance with the present invention, a significant decrease in insoluble aggregates was observed when 0.1% Tween-80 was added to a solution containing 2 g/L solids and 35% DPPC in 70% ethanol. As shown below in Table 14, insoluble aggregates reduced from 9.0% to 2.0% with the addition of 0.1% Tween-80.

TABLE 14

| Lot Number | HMW Protein | Insoluble Aggregates | Organic, Excipient, Mixing |
|---|---|---|---|
| 3-10697 | 3.9% | 9.0% | 70%, EtOH, static |
| 3-10697 | 6.6% | 2.0% | 70%, EtOH, 0.1% Tween-80, static |

Preparation of Dry Particles Containing Insulin

Particles with a formulation containing insulin, DPPC, and sodium citrate were prepared using apparatus substantially as shown in FIG. 2, and as described above for hGH. The resulting particles contained 60 wt % DPPC, 30 wt % insulin, and 10 wt % sodium citrate. A 1 L total combination volume was used, with a total solute concentration of 3 g/L in 60/40 ethanol/water. The aqueous solution was prepared as follows. 630 mg of citric acid monohydrate was added to 1.0 L of USP water to form 1.0 L of 3.0 mM citrate buffer. The pH was adjusted to 2.5 with 1.0 N HCl. 900 mg insulin was dissolved in 400 mL of the citrate buffer. The pH was adjusted to pH 6.7 using 1.0 N NaOH. The organic solution was prepared by dissolving 1.8 g of DPPC in 600 mL of ethanol. 400 mL of water was added to the organic solution for a total volume of 1 L.

The aqueous insulin solution and the organic solution were combined in a static mixer, such as static mixer 230. The outflow of the static mixer flowed into rotary atomizer 240, and the resulting atomized droplets were spray dried in spray dryer 250. The resulting 60 wt % DPPC, 30 wt % insulin, and 10 wt % sodium citrate particles were collected from bag house 260 into a container.

In order to obtain dry particles of particular physical and chemical characteristics, in vitro characterization tests can be carried out on the finished dry particles, and the process parameters adjusted accordingly, as would be apparent to one skilled in the art. Alternatively, particles containing 60 wt % DPPC, 30 wt % insulin, and 10 wt % sodium citrate could be produced using the apparatus substantially as shown in FIG. 6. In this manner, the desired aerodynamic diameter, geometric diameter, and particle density could be obtained for these particles in real-time, during the production process.

Preparation of Dry Particles Containing Humanized Monoclonal IgG1 Antibody

Particles with a formulation containing humanized monoclonal IgG1 antibody and DPPC were prepared using apparatus substantially as shown in FIG. 2, and as described above for hGH. The resulting particles contained 80 wt % humanized monoclonal IgG1 antibody and 20 wt % DPPC. A 2 L total combination volume was used, with a total solute concentration of 1.0 g/L in 30/70 ethanol/water. The aqueous solution was prepared as follows. 25.0 mL of 47.8 mg/mL humanized monoclonal IgG1 antibody solution was added to 1400 mL of USP water. The organic solution was prepared by mixing 0.8 g DPPC with 600 mL of ethanol.

The aqueous solution and the organic solution were combined in a static mixer, such as static mixer 230. The outflow of the static mixer flowed into rotary atomizer 240, and the resulting atomized droplets were spray dried in spray dryer 250. The resulting particles were collected from bag house 260 into a container.

In order to obtain dry particles of particular physical and chemical characteristics, in vitro characterization tests can be carried out on the finished dry particles, and the process parameters adjusted accordingly, as would be apparent to one skilled in the art. Alternatively, particles containing 80 wt % humanized monoclonal IgG1 antibody and 20 wt % DPPC could be produced using the apparatus substantially as shown in FIG. 6. In this manner, the desired aerodynamic diameter, geometric diameter, and particle density could be obtained for these particles in real-time, during the production process.

Preparation of Dry Particles Containing Epinephrine

Particles with a formulation containing epinephrine and leucine were prepared using apparatus substantially as shown in FIG. 2, and as described above for hGH. The resulting particles contained 18 wt % epinephrine bitartrate and 82 wt % leucine. An aqueous solution was prepared as follows: 900 mg epinephrine bitartrate and 4.1 g leucine were added to 300 mL of USP water and dissolved by stirring.

The 300 mL of aqueous solution and 700 mL of ethanol were combined in a static mixer, such as static mixer 230. This resulted in spray drying a 1.0 liter total combination volume, with a total solute concentration of 5.0 g/L in 70/30 ethanol/water. The outflow of the static mixer flowed into an atomizer, such as rotary atomizer 240, at an atomization rate of 19.5 g/min and a feed rate of 65 ml/min. The resulting atomized droplets were spray dried using dry nitrogen as the drying gas in spray dryer 250. The resulting particles were collected from bag house 260 into a container.

In order to obtain dry particles of particular physical and chemical characteristics, in vitro characterization tests can be carried out on the finished dry particles, and the process parameters adjusted accordingly, as would be apparent to one skilled in the art. Alternatively, particles containing 18 wt % epinephrine and 82 wt % leucine could be produced using the apparatus substantially as shown in FIG. 6. In this manner, the desired aerodynamic diameter, geometric diameter, and particle density could be obtained for these particles in real-time, during the production process.

Preparation of Dry Particles Containing Salmeterol Xinafoate

Particles with a formulation containing salmeterol xinafoate, leucine, and DSPC were prepared using apparatus substantially as shown in FIG. 2, and as described above for hGH. The resulting particles contained 74.55 wt % DSPC, 24 wt % leucine, and 1.45 wt % salmeterol xinafoate. A 1 L total combination volume was used, with a total solute concentration of 1.0 g/L in 70/30 ethanol/water. The aqueous solution was prepared as follows. 240 mg leucine was dissolved in 300 mL of USP water. The organic solution was prepared by dissolving 745.5 mg DSPC in 700 mL of ethanol. 14.5 mg salmeterol xinfoate was dissolved in the DSPC/ethanol solution. Both solutions were separately heated to 50° C.

The aqueous solution and the organic solution were combined in a static mixer, such as static mixer 230. The outflow of the static mixer flowed into rotary atomizer 240, and the resulting atomized droplets were spray dried in spray dryer 250. The resulting particles were collected from bag house 260 into a container.

In order to obtain dry particles of particular physical and chemical characteristics, in vitro characterization tests can be carried out on the finished dry particles, and the process parameters adjusted accordingly, as would be apparent to one skilled in the art. Alternatively, particles containing 74.55 wt % DSPC, 24 wt % leucine, and 1.45 wt % salmeterol xinafoate could be produced using the apparatus substantially as shown in FIG. 6. In this manner, the desired aerodynamic diameter, geometric diameter, and particle density could be obtained for these particles in real-time, during the production process.

Preparation of Dry Particles Containing Other Active Agents

Based upon the above examples and description, it would be readily apparent to one skilled in the art how to prepare dry particles containing other active agents using the methods and apparatus of the present invention. For example, the apparatus of FIGS. 2 and 6 could be used to prepare dry particles containing a combination of salmeterol and ipatroprium bromide in substantially the same manner as described above for salmeterol. The apparatus of FIGS. 2 and 6 can also be used, for example, to prepare dry particles containing albuterol sulfate, DPPC, DSPC, and leucine. The aqueous solution would be prepared by dissolving 200 mg leucine in 300 mL water to form an aqueous phase, and dissolving 40 mg of albuterol sulfate in the aqueous phase to form the aqueous solution. The organic solution would be prepared by dissolving 380 mg DPPC in 700 mL of ethanol to form an organic phase, and dissolving 380 mg DSPC in the organic phase to form the organic solution. The aqueous solution and the organic solution would be heated separately to 50° C. The aqueous solution and the organic solution would be combined in a static mixer, such as static mixer 230. The outflow of the static mixer would flow into rotary atomizer 240, and the resulting atomized droplets would be spray dried in spray dryer 250. The resulting particles would be collected from bag house 260 into a container. The resulting particles would contain 38 wt % DPPC, 38 wt % DSPC, 20 wt % leucine, and 4 wt % albuterol sulfate.

Conclusion

While various embodiments of the present invention have been described above, it should be understood that they have been presented by way of example only, and not limitation. The present invention is not limited to the preparation of dry particles for inhalation, nor is it limited to a particular active agent, excipient, or solvent, nor is the present invention limited to a particular scale, batch size or particle size. Thus, the breadth and scope of the present invention should not be limited by any of the above-described exemplary embodiments, but should be defined only in accordance with the following claims and their equivalents.

What is claimed is:

1. A method for preparing a dry powder composition, comprising:

combining a first phase and a second phase in a static mixer to form a combination wherein the first phase comprises human growth hormone and sodium phosphate, and the second phase comprises ethanol and ammonium bicarbonate;

atomizing the combination to produce droplets; and drying the droplets to form dry particles.

2. The method of claim 1, wherein the second phase further comprises 1,2-dipalmitoyl-sn-glycero-3-phosphocholine (DPPC).

3. A dry powder composition prepared by the method of claim 1.

4. The dry powder composition of claim 3, wherein the dry particles consist essentially of 93.5% human growth hormone and 6.5% sodium phosphate by weight of total human growth hormone and sodium phosphate.

5. A dry powder composition prepared by the method of claim 1, wherein the dry particles consist essentially of 80% human growth hormone, 6% sodium phosphate, and 14% DPPC by weight of total human growth hormone, sodium phosphate, and DPPC.

6. A unit dose of a dry powder composition comprising a unit dose receptacle having a therapeutically effective amount of dry powder composition formed according to the method of claim 1.

* * * * *